US008404256B2

(12) United States Patent
McCanless et al.

(10) Patent No.: US 8,404,256 B2
(45) Date of Patent: Mar. 26, 2013

(54) BIOMATERIAL COMPOSITE COMPOSITION AND METHOD OF USE

(75) Inventors: Jonathan Dempsey McCanless, Memphis, TN (US); Warren Ollver Haggard, Bartlett, TN (US)

(73) Assignee: The University of Memphis Research Foundation, Memphis, TN (US)

( * ) Notice: Subject to any disclaimer, the term of this patent is extended or adjusted under 35 U.S.C. 154(b) by 0 days.

(21) Appl. No.: 13/462,075

(22) Filed: May 2, 2012

(65) Prior Publication Data

US 2012/0282302 A1 Nov. 8, 2012

Related U.S. Application Data

(60) Provisional application No. 61/483,446, filed on May 6, 2011.

(51) Int. Cl.

| | |
|---|---|
| ***A61K 47/36*** | (2006.01) |
| ***A61K 35/14*** | (2006.01) |
| ***A61K 9/00*** | (2006.01) |
| ***A61K 38/18*** | (2006.01) |
| ***A61P 19/00*** | (2006.01) |
| ***A61P 29/00*** | (2006.01) |
| ***B65D 85/00*** | (2006.01) |

(52) U.S. Cl. ..................... 424/400; 424/532; 206/524.1; 514/7.6; 514/770

(58) Field of Classification Search ........................ None
See application file for complete search history.

(56) References Cited

U.S. PATENT DOCUMENTS 5,482,932 A 1/1996 Thompson
2005/0003010 A1 * 1/2005 Cohen et al. .................. 424/486
2005/0186240 A1 * 8/2005 Ringeisen et al. ............ 424/423
2006/0096504 A1 5/2006 Grover et al.
2006/0148704 A1 * 7/2006 Schense et al. ................. 514/12
2006/0153896 A1 7/2006 Chu et al.
2006/0159823 A1 7/2006 Melvik et al.
2007/0059281 A1 3/2007 Moseley et al.
2008/0279944 A1 11/2008 Sawhney et al.
2009/0142305 A1 * 6/2009 Zhang .......................... 424/93.7
2010/0021544 A1 1/2010 Bourges et al.
2010/0080788 A1 4/2010 Barnett et al.

OTHER PUBLICATIONS

Tan, et al.; Preparation and characterization of an injectable composite; J Mater Sci: Mater Med (2009) 20:1245-1253; DOI 10.1007/s1086.

Matsuno, et al.; Preparation of injectable 3D-formed β-tricalcium phosphate bead/alignate composite for bone tissue engineering; Dental Materials Journal 2008: 27 (824-834).

Tan, et al.; In vitro and in vivo degradation of an injectable bone repair composite; Polymer Degradation and Stability 95 (2010) 1736-1742.

International Searching Authority—PCT; International SearchReport; Nov. 5, 2012.

* cited by examiner

*Primary Examiner* — Robert A Wax
*Assistant Examiner* — Randeep Singh
(74) *Attorney, Agent, or Firm* — Harris, Shelton, Hanover & Walsh

(57) ABSTRACT

This invention relates to a process to facilitate osteochondral bone remodeling in a subject by inducing regeneration of this bone to a healthy, vascularized state capable of supporting the underlying hyaline cartilage of articular joints and spinal discs, both biomechanically and metabolically and to deliver a bioactive agent. This process involves the steps of: administering an effective amount of an injectable in situ curing biomaterial composite to a site. The biomaterial composite product is prepared by a process involving the steps: admixing an alginate solution with a nonporous aggregate of β-tricalcium phosphate, in a sufficient amount to initiate polymerization of the alginate solution, to form a hydrogel having from between 10 to 20 percent by volume of β-tricalcium phosphate.

40 Claims, 12 Drawing Sheets

Fold Change with Time Compared to
Undifferentiated Mesenchymal Stem Cells
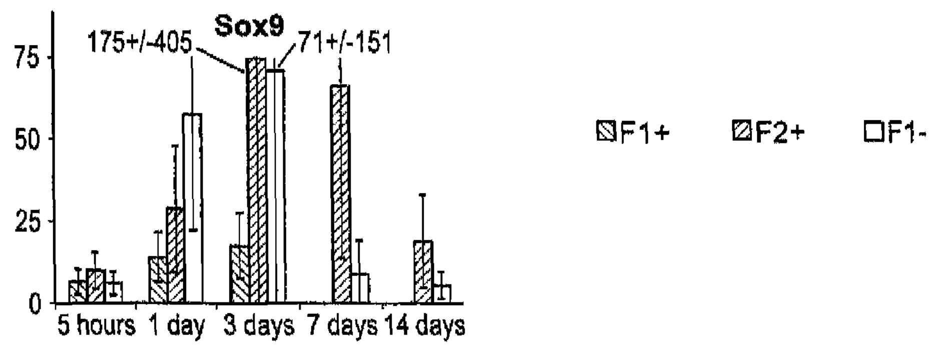
FIG. 3A
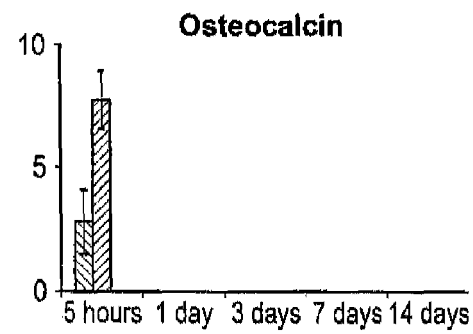
FIG. 3C
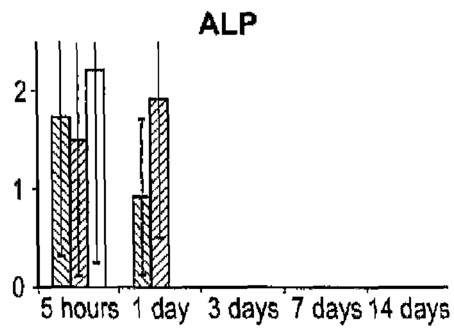
FIG. 3D
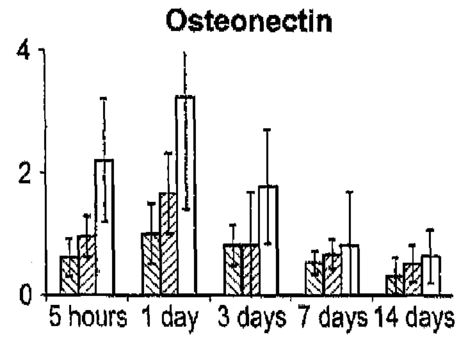
FIG. 3E
Runx2
10
5
0
5 hours 1 day 3 days 7 days 14 days
FIG. 3B

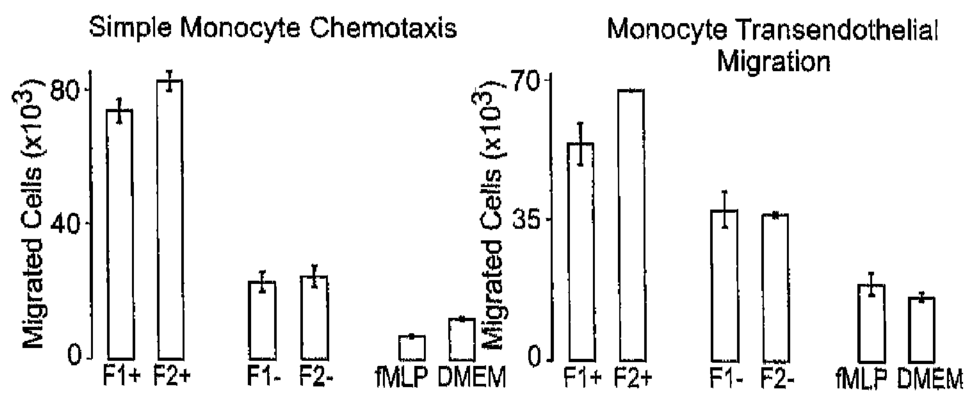
FIG. 6A
FIG. 6B
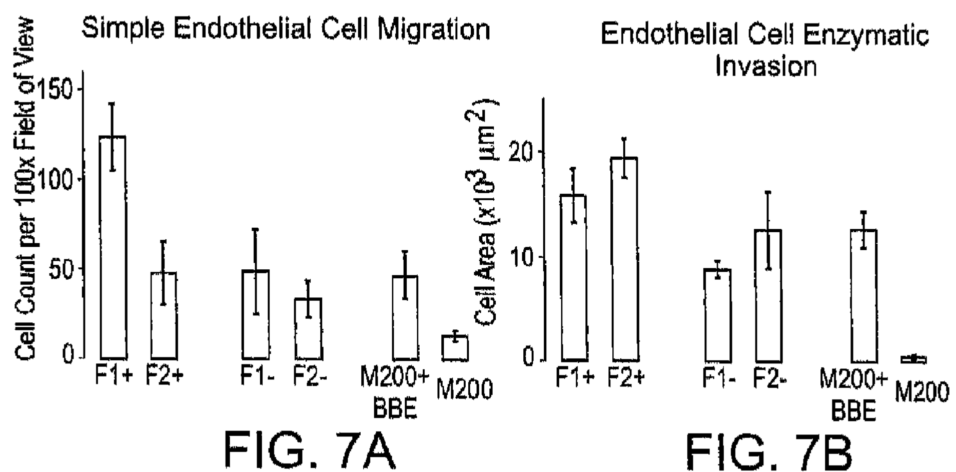
FIG. 7A
FIG. 7B

SEQUENCE LISTING

```
<160> NUMBER OF SEQ ID NOS: 6

<210> SEQ ID NO 1
<211> LENGTH: 24
<212> TYPE: DNA
<213> ORGANISM: Murine

<400> SEQUENCE: 1

taggtcgatg cacaactggg tgaa                                            24


<210> SEQ ID NO 2
<211> LENGTH: 24
<212> TYPE: DNA
<213> ORGANISM: Murine

<400> SEQUENCE: 2

tctttgacgc tcggaactgt agca                                            24


<210> SEQ ID NO 3
<211> LENGTH: 23
<212> TYPE: DNA
```

```
<213> ORGANISM: Murine

<400> SEQUENCE: 3

tattgctcaa tctcgggtgc tga                                       23


<210> SEQ ID NO 4
<211> LENGTH: 24
<212> TYPE: DNA
<213> ORGANISM: Murine

<400> SEQUENCE: 4

ccagagcgaa agcatttgcc aaga                                      24


<210> SEQ ID NO 5
<211> LENGTH: 24
<212> TYPE: DNA
<213> ORGANISM: Murine

<400> SEQUENCE: 5

actcctgctt gctgatccac atct                                      24


<210> SEQ ID NO 6
<211> LENGTH: 24
<212> TYPE: DNA
<213> ORGANISM: Murine

<400> SEQUENCE: 6

tcgtaccaca ggcattgtga tgga                                      24
```

BIOMATERIAL COMPOSITE COMPOSITION AND METHOD OF USE

RELATED APPLICATIONS

This application claims the benefit of U.S. provisional patent application filed May 6, 2011 Ser. No. 61,483,446 under 35 USC §119(e) (hereby incorporated by reference).

STATEMENT REGARDING FEDERALLY SPONSORED RESEARCH OR DEVELOPMENT

None

REFERENCE TO SEQUENCE LISTING, A TABLE, OR A COMPUTER PROGRAM LISTING COMPACT DISC APPENDIX

Sequentially uploaded as a file.

FIELD OF THE INVENTION

The present invention relates to an injectable biomaterial composite, a method to make the biomaterial composite, and a method to use this biomaterial composite in medical applications.

BACKGROUND OF THE INVENTION

Bone damage and damage to associated tissues from less severe injury can typically heal naturally. Other damage from more severe injuries to bone and related tissues caused by extreme trauma and complications associated with disease or genetic conditions, often require surgery, tissue grafts, or artificial implants in order to reconstruct these tissue in order to reestablish function or reduce associated pain. The reconstruction results from these interventions are often less than ideal. Engineered biomaterial composites can be developed to produce a biological function beyond that which naturally exists or is compromised due to injury or disease.

For example, there are 23 discs in the human spine. Discs have an outer annulus fibrosus, which surrounds an inner nucleus pulposus. The annulus fibrosus is made of several layers of fibrocartilage. The nucleus pulposus contains loose fibers suspended in a mucoprotein gel with a consistency of jelly. The nucleus of the disc acts as a shock absorber, absorbing the impact of the body's daily activities and keeping the vertebrae separated. In certain conditions, the jelly nucleus pulposus is forced out of its natural anatomical location and may apply pressure to or induce inflammation in nerves or nerve ganglia local to the disc.

Degeneration-related and trauma-induced damage to the spinal discs are currently treated with cells, growth factors, injectable materials, such as silicone fluid or elastomer, or surgical procedures such as tissue removal in conjunction with or without spinal implants which often induce vertebral fusion. Generally, repair of damaged disc as functional living tissue is difficult. The cause of disc degeneration has been speculated to be a resultant of poor disc nutrient supply and waste removal. The inner nucleus pulposus of the disc is largely nourished and relieved of metabolites by transport through the upper and lower vertebral endplates and less so through the annulus fibrosus. Various medical conditions, such as sclerosis, damage the vertebral endplates and limit diffusion to and from the disc. This lack of transport to and from the disc likely impedes present regenerative treatment systems in the repair of damaged discs. This disease etiology is paralleled in other joints as well. Diffusion limiting changes in the calcified and vascular tissues of subchondral and cancellous bone precede the onset of osteoarthritic joint failure in diarthrodial joints as well.

Osteoarthritic degenerative joint disease and disorders of the spinal column (discs and vertebrae) accounted for an estimated 815,000 and 634,000 US diagnoses in discharged inpatients, respectively, during 2007. These occurrences were ranked fourth and ninth in prevalence, excluding pregnancy and childbirth related instances, and resulted in a financial burden of $20.2 billion (inflation-adjusted hospital costs). Levit K W, L. Stranges, E. Ryan, K Elixhauser, A, *HCUP Facts and Figures: Statistics on Hospital-based Care in the United States,* 2007. 2009, Agency for Healthcare Research and Quality: Rockville, Md. Degeneration is associated with an overwhelming majority of these cases, and as such arthroplasty, in the case of diarthrodial joints, and surgical-induced ankylosis for vertebral fusion are the most common interventions employed for these unsalvageable joints. *Spine: Low Back and Neck Pain, in United States Bone and Joint Decade: The Burden of Musculoskeletal Diseases in the United States.* 2008, American Academy of Orthopaedic Surgeons: Rosemont, Ill.

Joint prostheses have an obvious advantage over fusion due to at least a partially preserved functionality, but both clinical treatments are plagued with exorbitant costs, native tissue morbidity, and extensive rehab/recovery, and they may lead to unforeseen complications and traumatic revision surgery. This outcome present needs for improved, economical treatment modalities. especially in regard to the disc. Khan S N, and Stirling A J. Controversial topics in surgery: degenerative disc disease: disc replacement. Against. *Ann R Coll Surg Engl* 2007; 89(1): p. 6-11. Wilson-MacDonald J, and Boeree N. Controversial topics in surgery: degenerative disc disease: disc replacement. For. *Ann R Coll Surg Engl* 2007; 89(1): p. 6-11. Although the pains and costs associated with the treatment of diarthrodial joints such as hips and knees is evident through the long road of pain management leading to arthoplasty. Hunter D J, and Lo G H. The management of osteoarthritis: an overview and call to appropriate conservative treatment. *Rheum Dis Clin N Am* 2008; 34: p. 689-712. Surgeons, scientists, and engineers have made many attempts to restore functional, biomechanically stable cartilage within these articulating joints through grafting procedures with little to no repeatable success. Revell C M, and Athanasiou K A. Success rates and immunologic responses of autogenic, allogenic, and xenogenic treatments to repair articular cartilage defects. *Tissue Eng Part B Rev* 2009; 15(1): p. 1-15.

Use of resorbable, regenerative synthetic biomaterial composites within joints is an attractive possibility but, has traditionally performed less effectively than grafting and results have been highly variable. Although initial success is common, osteochondral grafting (allogenic tissue graft) commonly fails long-term. These inconsistent and failed attempts suggest the underlying causes of cartilage degeneration are not being circumvented by these clinical practices and researched treatments. Accompanying joint degeneration, and manifesting prior to complete cartilage failure, is a change in the underlying subchondral and cancellous bone. Most notably is advancing calcified cartilage (tidemark) early in the disease, and osteophyte formation around invading vessels in the advanced state. Goldring S R. The role of bone in osteoarthritis pathogenesis. *Rheum Dis Clin North Am* 2008; 34(3): p. 561-71. Accompanying abnormal subchondral plate thickness, adjacent trabecular bone mineral density increases with alterations in architecture, resulting in brittleness. Id. Within the knee and hip, bone may become necrotic in severe cases, eventually collapsing under physiological loading, resulting in destruction of the articular surface. Bancroft L W, Peterson J J, and Kransdorf M J. Cysts, geodes, and erosions. *Radiol Clin North Am* 2004; 42(1): p. 73-87. Carrino J A, Blum J, Parellada J A, Schweitzer M E, and Morrison W B. MRI of bone marrow edema-like signal in the pathogenesis of subchondral cysts. *Osteoarthritis Cartilage* 2006; 14(10): p. 1081-5. In the spine, the vertebral cortex thickens adjacent to the disc, causing occlusion of vascular supplied diffusion pathways which link the disc to the surrounding vertebral bodies. Adams M A, and Roughley P J. What is intervertebral disc degeneration, and what causes it? *Spine* 2006; 31(18): p. 2151-61.

It is reasonable to believe that this loss of a nutrient pathway across the vertebral cortex and endplate to the disc or across subchondral bone in articulating joints leads to the cellular apoptosis and tissue turnover associated with early stages of joint degenerative; later, osteophytes and vessels invade, bringing nerve ending and the associated pains. A technique to restore this nutrient pathway solves a long standing need in the medical field of subchondral bone associated with diarthrodial and endplates and vertebral cortex and endplate associated with spinal discs.

BRIEF SUMMARY OF THE INVENTION

This invention provides a biomaterial composite composition. This composition is made of an alginate hydrogel having embedded therein nonporous β-tricalcium phosphate aggregates having a diameter of between 125-150 μm and a bioactive agent. In the preferred embodiment the bioactive agent is derived from platelets and the bioactive agent is at least 50 percent by volume of the hydrogel. Additionally, the composition can also include calcium distributed throughout the matrix of the hydrogel.

In another embodiment, a kit is provided with a first mixing container containing an alginate solution, connectable to a second mixing container. The second mixing container includes at least one calcium salt, in a sufficient amount to initiate polymerization of the alginate solution to form a hydrogel, wherein the calcium salt is nonporous β-tricalcium phosphate. In this embodiment, either the first or the second container is connected to a needle of dimensions not larger than that of a 16 gauge needle.

The examples show the use of these composites as cost efficient, robust bone graft substitutes. Most notably is the application for the enhancement of nonunion, necrosis, and cyst osteo-therapies. Additionally, these composites have the ability to remodel withstanding, yet unhealthy, osseous tissue as is seen adjacent to vertebral and diarthrodial joints prone for arthritic degeneration and highlight the possibilities of an early preventative remodeling therapy. Furthermore, closure of nonunion fracture ends and bone cyst perimeters are typically of a cortical nature. Therefore, an implant system capable of inducing both resorption of unhealthy bone and formation of healthy bone is warranted, and these events describe the potential of the alginate/platelet releasate/$CaPO_4$ system.

In one embodiment, this invention relates to a method to facilitate bone repair by administrating to a mammalian subject in need of treatment an effective amount of the composition of this invention. More specifically, this method involves facilitating osteochondral bone remodeling in a subject by inducing regeneration of this bone to a healthy, vascularized state capable of supporting the underlying hyaline cartilage of articular joints and spinal discs, both biomechanically and metabolically. This process involves the steps of: administering an effective amount of an injectable in situ curing biomaterial composite. The biomaterial composite product is prepared by a process involving the steps of admixing an alginate solution with at least one calcium salt, in a sufficient amount to initiate polymerization of the solution to form a hydrogel, wherein the calcium salt is nonporous β-tricalcium phosphate. The product can also include a calcium salt, such as calcium sulfate to provide an additional source of calcium to the hydrogel.

This invention, in another embodiment, provides a process to release a bioactive agent or agents to a subject. In particular, this process involves the steps of administering an effective amount of an injectable in situ curing biomaterial composite to the subject. The material is prepared by a process involving the steps of admixing an alginate solution with a sufficient amount of a bioactive agent and least one calcium salt, in a sufficient amount to initiate polymerization of the solution, to form a hydrogel, wherein the calcium salt is a nonporous β-tricalcium phosphate. The inflammatory mediated response associated with a fracture repair can be modulated by changing the ratios within the biomaterial composite.

In another embodiment, this invention provides a method of treating a condition whose effects can be reduced by stimulating the cellular responses induced by platelet releasate exposure. This method involves administering to a subject in need of treatment a therapeutically effective amount of a biomaterial composite composition. The biomaterial composite composition is made of a hydrogel formed from an alginate gel having embedded therein nonporous β-tricalcium phosphate solid phase, and a bioactive agent, wherein the bioactive agent is derived from platelets.

BRIEF DESCRIPTION OF THE SEVERAL VIEWS OF THE DRAWINGS

FIG. 3A-I shows Sox 9, Runx2, Osteocalcin, ALP, Osteonectin, Aggrecan, Collagen I, CD105, and Fibroblast-specific Protein mRNA fold change in MSCs grown on the various compositions compared to second passage MSCs in monolayer over time. B-actin was taken as the housekeeping gene, and mesenchymal stem cells (MSCs) at time zero were taken as baseline (y=1).

FIG. 6A shows simple chemotaxis results of TIB-71 RAW 264.7 monocytes with average values with error bars indicating plus/minus one standard deviation.

FIG. 6B shows human umbilical vein endothelial cell (HUVEC) tranendothelial migration by TIB-71 RAW 264.7 monocytes with average values with error bars indicating plus/minus one standard deviation.

FIG. 7A shows the simple migration of HUVECs. Data show average values with error bars indicated plus/minus one standard deviation.

FIG. 7B (right) shows enzymatic-driven HUVEC invasion (haptotaxis) through basement membrane gels. Data show average values with error bars indicating plus/minus one standard deviation.

DETAILED DESCRIPTION OF THE INVENTION

Figure 1:
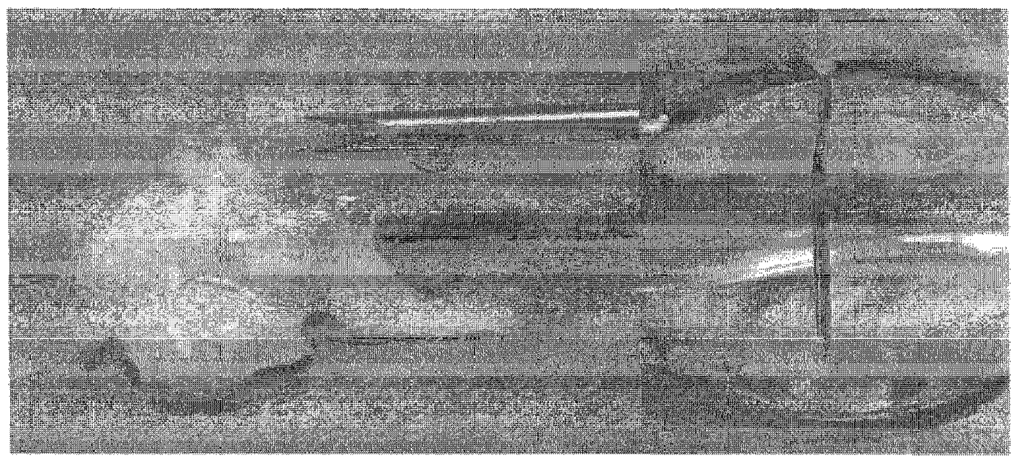
FIG. 1 Shows composition 1 with water substituted for concentrated platelet releasate being injected from 16-gauge needle in air and phosphate buffered saline showing consolidation of ejected gel.

Now referring to FIG. 1, an injectable, in situ-curing, alginate-based hydrogel is shown. These alginate-based hydrogels can be used in a process for remodeling diseased osteochondral bone to that of a healthy state, evading the progression of joint degeneration in one aspect, or can be applied to an injured or diseased osseous site within a subject to facilitate healing.

This biomaterial composite can be used to repair and or regenerate bone and its associated tissues, such as marrow, vasculature and or adjacent cartilage, ligament or tendon, subchondral or cancellous bone, and spinal disc or to deliver other bioactive agents for other medical applications. More specifically, the biomaterial composite can be injected into a site in a subject. This site can be bone adjacent to cartilage; such as, for example, articular cartilage of an articulating joint, in the knee and hip. The cartilage can include articular and fibrocartilage. It can be injected into and adjacent to endplates of vertebral disc, with the intention of remodeling the underlying subchondral bone to a healthy, vascularized state. The biomaterial composite can be delivered to bone by drilling hole with a drill bit or other tool such as a jamshidi (bone needle) accessing the subchondral and cancellous bone adjacent to upper and lower vertebral endplates and annulus fibrosus of a spinal disc or articular cartilage in articulating joints and the biomaterial composite can be delivered through this hole or opening in the bone. The biomaterial composite can be delivered adjacent to or into cartilage. The subject includes mammals, such as humans, equines, canines, etc. The present invention also provides a biomaterial composite for the controlled delivery of bioactive agents.

The composite scaffolds are primarily made of an alginate hydrogel with dense nonporous micron-scale β-tricalcium phosphate aggregates. See, e.g. U.S. Pat. No. 7,754,246. Dense nonporous micron-scale β-tricalcium phosphate aggregate is a particulate. The aggregate particles contain a minimal amount of porosity which is generally achieved through a sintering process (typically between 1180-1450 degrees Centigrade, preferably at 1300-1400 degrees Centigrade) of smaller (typically sub-micron) sized particles from a green (unsintered) particle to a consolidated (continuous solid) particle. Other methods of production may include producing a calcium phosphate melt which would solidify to a continuous solid. This solid construct could then be processed to through milling, grinding, or other fragmentation techniques alone or in combination with a sieving or separation process to generate/collect particles of a desired size. The solid construct may be of the β-tricalcium phosphate crystalline phase or the processed particles could be refired to induce formation of such phase before or after the sieving/separation process. These sintered particles, however produced, approach the theoretical density and theoretical mechanical properties of the β-tricalcium phosphate crystal lattice structure. Variation from theoretical values is a result of minor imperfections (cracks, doped elements (such as silicon), and/ or pores) in the continuous crystal/solid structure. Aggregate may be defined as a component of a composite material which acts to increase the bulk volume of a composite and/or add or alter mechanical strengths of the composite; examples of such are the addition of sand and gravel aggregate to concrete and the addition of carbon fiber aggregate to a polymer composite.

In the preferred embodiment, the diameter of the β-tricalcium phosphate aggregates ranges from between 125-150 μm. The diameter of the β-tricalcium phosphate aggregates can be adjusted by one skilled in the art depending on the injection canula geometries. The β-tricalcium phosphate granule aggregates provide an osteoconductive scaffold for the bone remodeling process; as the hydrogel is resorbed, the aggregates are exposed to the surrounding and invading tissue. Calcium containing setting agents may be powder and or particulate form.

β-tricalcium phosphate volume percent of the composite can be altered to optimize implant for optimal bone regeneration conditions, as bone mineral density varies among locations within and between bones so that different values are presented due to the varying presence of other osseous related tissue such as vasculature and marrow.

The alginate hydrogel serves as a diffusion barrier for the release of bioactive agents, carrier of the osteoconductive aggregates and bioactive agents to the implant site, localizes the implant and osteoconductive aggregates, and degrades relatively early after implantation, such as one to four weeks after implantation. As the hydrogel degrades the slower degrading osteoconductive aggregates are presented at the hydrogel degradation front, ideal for the "creeping substitution" nature of regenerating bone with bone grafts and bone graft substitutes.

The hydrogel is an alginate solution composed of alginic acid. The alginic acid is made of a monovalent salts of alginic acid, such as sodium alginate or potassium alginate Polymer weight percent of the hydrogel can be altered to control release kinetics.

Calcium phosphate serves as the scaffold for angiogenesis and osteogenesis. Calcium sulfate serves as the major source of calcium ions to induce the setting reactions. The calcium component provides a tissue-engineered scaffolding material for angiogenesis and osteogenesis. For example, calcium sulfate can be added to the composition to provide the calcium component. Similarly, calcium sulfate provides a high surface area for calcium dissolution into the matrix. Calcium sulfate dissolves much faster and has a much higher solubility than does calcium phosphate (for example). In the preferred embodiment, calcium is derived from a calcium salt and/or base having an elemental calcium mass in grams to hydrogel volume in milliliters, wherein a ratio ranges from 0.00238 to 0.00076824. Additionally, in the preferred embodiment, the calcium source is derived from calcium sulfate dihydrate. Calcium sulfate dihydrate has an elemental calcium mass is 23.28 percent of the calcium sulfate dihydrate mass.

Alpha hydroxy carboxylic acids or salts thereof may also be incorporated to improve flowability and setting characteristics in some embodiments, as a slower curing material is easier to inject. The alpha hydroxy carboxylic can be either solution or salt form.

Bioactive agents may be added during mixing for in vivo delivery and controlled release of bio-agents. The biomaterial composite is designed to be mixed in a sterile surgical setting and delivered as a sol through a minimally invasive means (injection) to an osseous site where it gels for intentions of repair and/or regeneration of bone and its associated tissues (marrow, vasculature, and/or adjacent cartilage, ligament, or tendon). This bone grafting material can also be used for osseointegration, such as required during arthroplasty (hip, knee, disc, ankle, elbow and shoulder), dental implants, and attachment (tendon, ligament, cartilage (hyaline and fibro)). Additionally, the biomaterial composite can be used for athrodesis, such as athrodesis across diarthrodial joints of hips, knees, wrists, and ankles, or amphiarthrodial joints of the spine.

The term "angiogenic" means a agent causing the physiological process involving the growth of new blood vessels.

The term "annulus fibrosus" means fibrous ring of intervertebral disc; the circumferential ring-like portion of an intervertebral disc.

The term "articular cartilage" means the cartilage covering the articular surfaces of the bones participating in a diarthrodial/synovial joint.

The term "hyaline cartilage" may be used to describe a cartilage which is rich in collagen type II such as the vertebral endplate and articular cartilage.

The term "bioactive agent" may include an agent having bioactivity such as, for example, angiogenic, osteoinductive, osteoconductive, or pharmaceutical agents. Therefore, bioactive agents may include for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholnergics, anticholinergics, antispasmodics, antiulcer agents, skeletal and smooth muscle relaxants, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, antiarthritics, drugs can include, for example, hyaluronate, vitamin D, Statins, vitamin K and bisphosphonates, or muscone (She Xiang) and salt, metabolites, derivate thereof; and progenitor cells, such as stem cells; natural and recombinant growth factors, and exogenous growth factors including for example: transforming growth factor β- (TGF-B), platelet-derived growth factor (PDGF), insulin-like growth factor (IGF), sonic hedgehog (SHH), vascular endothelial growth factor (VEGF), bone morphogenetic proteins (BMPs), fibroblast growth factor (FGF) and parathyroid hormone (PTH)), alone or in various combinations.

The term "bioactivity" means the effect of a given agent, such as a vaccine, medicament, or growth factor upon a living organism, living tissue, or cells.

The term "fibrocartilage" means a kind of cartilage with a fibrous matrix and approaching fibrous connective tissue in structure.

The term "osteoinductivity" means acceleration or induction of new bone formation by chemical or biochemical process. A common test for osteoconductivity is the bone formation in a muscle pouch.

The term "osteoconductivity" refers to any structure that facilitates the formation of bone structure. Commonly used to describe the properties of various types of bone grafts and bone graft substitutes.

The term "osteogenic" refers to being related to bone be it growth factors, cell phenotype, or extracellular matrix.

The term "osteogenic differentiation" means cell phenotypes consistent of bone-forming (osteoblast) or bone-regulating (osteocyte) cells.

The term "platelet" is used here to refer to a blood platelet. A platelet can be described as a minuscule protoplasmic disk occurring in vertebrate blood. Platelets play a role in blood clotting. The platelet may be derived from any source including a human or mammalian blood supply, or the patient's own blood. Thus, the platelets in the composition of the inventions may be autologous i.e. from the same human treated with the composition or allogenic i.e. from a human but, not the same human being treated with the composition.

The term "platelet-rich-plasma," "PRP" and the like are used interchangeable here to mean a concentration of platelets in a carrier which concentration is above that of platelets normally found in blood. For example, the platelet concentration may be 5 times, 10 times, 100 times or more the normal concentration in blood. The PRP may use the patient's own plasma as the carrier and the platelets may be present in the plasma at a range of from about 200,000 or less to 2,000,000 or more platelets per cubic centimeter. The PRP may be formed from whole blood e.g. by technology disclosed for example in U.S. Pat. No. 5,614,106.

The term "platelet releasate" is the PRP as defined above but treated so that what is inside the platelet shells are allowed to come out. The releasate may be subjected to processing whereby the platelet cytoplasm are removed and/or other blood components are removed, e.g. white blood cells and/or red blood cells, fibrin clot, and/or remaining (or majority of) plasma is removed. The pH of the platelet releasate may be adjusted to physiological pH or other as needed.

The term "subchondral bone" means bone which provides support for the hyaline cartilage on the articular surface or in the endplate and annulus fibrosus/bone interface.

A "therapeutically effective" amount of the biomaterial composite composition is an effective amount of the biomaterial composite composition to stimulate bioactivity, such as for example cellular responses inducible by platelet releasate exposure.

In one embodiment, a biomaterial composite composition, referred to as Composition 1 is made of: 2 wt % alginate (as sodium alginate); 20 vol % 125-150 μm β-tricalcium phosphate granules; 50 vol % of gel phase is concentrated platelet releasate; 0.0100 calcium sulfate (as dihydrate) powder weight to gel phase volume ratio. In another embodiment, a biomaterial composite composition, referred to a Composition 2 is made of: 8 wt % alginate (as sodium alginate); 10 vol % 125-150 μm β-tricalcium phosphate granules; 50 vol % of gel phase is concentrated platelet releasate; 5 mM trisodium citrate in gel phase; 0.0033 calcium sulfate (as dihydrate) powder weight to gel phase volume ratio.

The implantable (ready for delivery) biomaterial composites are made by passing materials back and forth between two coupled mixing containers such as syringes. One syringe contains a sodium alginate solution at twice the final concentration, and the other syringe contains the calcium salts. Concentrate platelet releasate is either added directly to the calcium salt syringe (Composition 1) or combined with trisodium citrate in a separate syringe and then transferred to calcium salt syringe (Composition 2). The two syringes are then coupled together and materials are passed back and forth between the two, initiating the setting reaction. In this embodiment, the syringe has a volume of 3 cc. The syringe includes a means of attaching a needle.

The biomaterial composite is designed to be mixed in a sterile surgical setting and delivered as a sol through a minimally invasive means, such as an injection to an osseous site in a patient in need thereof, where it gels for intentions of repair and/or regeneration of bone and its associated tissues (marrow, vasculature, and/or adjacent cartilage, ligament, spinal disc or tendon). A therapeutically effective amount of the composition is an amount to cause the desired physiological effect, such as osteogenic differentiation. This biomaterial composite can be used in both medical and veterinarian applications.

Underlying changes in subchondral and cancellous bone precede joint degeneration in spinal discs, knees, hips, and other joints. To example this a preliminary fourteen-day growth and osteochondral differentiation studies demonstrated biocompatibility and bioactivity of the Compositions 1 and 2 in second passage rat marrow-derived mesenchymal stem cells seeded onto and around cured gels containing human concentrated platelet releasate.

This example introduced novel platelet releasate-containing alginate/calcium phosphate composites for this intervention therapy and evaluated them in vitro through mesenchymal stem cell biocompatibility and induction of osteochondral differentiation. DNA quantification and gene expression profiles suggested mesenchymal stem cells were directed along an osteochondral differentiation pathway, more specifically, to the immature nonhypertrophic chondrocyte phenotype. These conclusions were based on reduced mitogenic activity, a rapid upregulation followed by suppression of Runx2 transcription factor mRNA, sustained upregulation of Sox9 transcription-factor mRNA, and the absence of late marker expressions for both mature articular chondrocytes and osteoblasts over the course of fourteen days.

Example 1

Rat mesenchymal stem cells from two donors which had been cryopreserved upon reaching 80% confluence of primary cultures where combined at a 1:1 ratio and seeded at 10^4 cells/cm^2 in T-flasks. Cells were passaged at 80% of this first passage and used for experimentation upon again reaching 80%. At the beginning of each experiment MSCs from two donors were combined and expanded for one passage in monolayer and were entering their second passage. Cells were grown in 10% (v/v) FBS-supplemented DMEM-HG containing penicillin, streptomycin, and amphotericin under normal culture conditions (37° C.; 5% (v/v) $CO_2$; 100% RH).

Experimental Composition 1 and Composition 2 (Table 1) were formed in 3.6 ml and 3.3 ml sterile quantities, respectively. Calcium salts were loaded in to 3 cc syringes which were sterilized with gamma irradiation (~2.5 Mrad). Concentrated human platelet releasate (hCPR) and water were sterilized through 0.2 μm filtration. Alginate solutions at twice the final weight percentage (per Table 1) were autoclave sterilized for 15 minutes at 120° C. on the liquids setting (slow vent). Trisodium citrate was sterilized through 0.2 μm filtration as a solution followed by sterile lyophillization for reconstitution at time of mixing.

TABLE 1

| Compositions | | | | |
|---|---|---|---|---|
| Composition | Liquid | B-TCP* | Sodium Alginate** | Calcium Sulfate (L/P***) |
| 1 or F1+ | 50% (v/v) water; 50% (v/v) hCPR | 20 vol % | 2 wt % | 300 |
| 2 or F2+ | 50% (v/v) water; 50% (v/v) hCPR; 5 mM trisodium-citrate**** | 10 vol % | 8 wt % | 100 |

TABLE 1-continued

| Compositions | | | | |
|---|---|---|---|---|
| Composition | Liquid | B-TCP* | Sodium Alginate** | Calcium Sulfate (L/P***) |
| F1-Material Control | 100% (v/v) water | 20% | 2 wt % | 300 |

*Volume percent based on -β-tricalcium phosphate density of 3.14 g/cm^3
**wt % based on gel portion only
***L/P is equal to gel volume in milliliters divided by calcium sulfate mass in grams
****Molarity is based on gel volume only.

In a cell culture hood 1.5 ml of sterile alginate solution were loaded into a sterile 3 cc syringe. Sterile hCPR was added to a sterile 3 cc syringe containing the sterile calcium salts; in the case of Composition 2 the hCPR was first mixed with the appropriate amount of sterile, lyophilized trisodium citrate before being mixed with calcium salts. The alginate containing syringe was then coupled with the hCPR/calcium salt syringe and curing was initiated by passing the materials back and forth between the syringes 15-20 passes. All of the content was positioned in one syringe, junction broken, and 16-gauge needle added. 1 ml aliquots of the gel were spread completely over the surface of 12-well culture plate wells through injection. Gels were given a minimum 15 minutes to cure in air.

This resulted in an alginate-based composite system containing 125-150 μm β-tricalcium phosphate (TCP) aggregate. Osteoconductive granules (Plasma Biotal Ltd; Derbyshire, UK) were incorporated within a continuous alginate (Fluka; St. Louis, Mo.) hydrogel matrix. A small amount of Terra Alba calcium sulfate (USG; Chicago, Ill.) was included in each formulation to induce curing. hCPR was incorporated such that it accounted for half of the hydrogel volume in both experimental formulations and served as a source of biologically active molecules.

hCPR processing lots were acquired using an in-house centrifugal methodology under an Institution Review Board approved protocol and consisted of pools from four or five participants' draws. Processing was conducted in polypropylene containers. ~120 ml of blood was drawn from each individual into acid citrate dextrose formula A (ACD) and separated in 30 ml aliquots. Aliquots were spun at 160 g for ten minutes, and plasma and buffy coat were collected and separated into 10 ml aliquots. Platelets were then separated from the serum through further spinning at 2,000 g; serum was pulled off of each tube leaving 2 ml behind. Platelets were resuspended and pooled. Clotting was then induced by the addition of 50 μl 10% (wfv) calcium chloride per 1.2 ml platelet suspension. Clotting was performed for one hour at 37° C., and then the fibrin clot was removed from the releasate using a hypodermic needle to expel releasate incorporated within weakly contracted clots. hCPR was sterile filtered and stored at −80° C. in 1 ml aliquots until time of use.

All specimens were made using sterile material and originated from the same raw material lots, excluding hCPR which came from individual blood collection poolings for each experiment. The various components were mixed in syringes, and 1 ml of gel was delivered via a 16 gauge needle to 12-well culture plates where gel discs were allowed to cure prior to adding medium and MSCs to the wells.

Cell proliferation was assessed through lysate DNA quantity measures using the QUANT-IT PICOGREEN DSDNA KIT (Invitrogen Corp; Carlsbad, Calif.) per the manufacturer's instructions. Specimen values were taken as the average of duplicate measures. $5\times10^4$ MSCs were seeded onto F1+ and F2+ experimental material surfaces and standard tissue culture plastic (TCP) for monolayer expansion in polystyrene tissue culture plates (Corning; Corning, N.Y.). Cultures were allowed to expand for zero, three, seven, and fourteen days on the material surfaces and the manufacturer treated plastic surface. Cultures were maintained under the same medium and environmental conditions described above, and 2.2 ml medium per well was refreshed every three or four days. Cell lysates from each condition (material and time point) were collected (n=3); nine $5\times10^4$ MSC specimens were taken for time zero, allowing for a balanced experimental design. Collection protocols varied due to release of cells from the materials becoming more challenging with time in culture. Media was first aspirated from the wells and specimens were rinsed with HBSS. MSCs were easily collected from TCP control wells via mild trypsinization in the presence of ethylenediaminetetraacetic acid (EDTA). Cells were collected from experimental materials through multiple treatments with varying concentrations of trypsin, never exceeding 2.5% (w/v), in the absence of EDTA, avoiding dissolution of the hydrogels. Collected cells were pelleted and lysed in deionized water. Lysates were stored at −80° C. until time of analysis.

MSC differentiation along osteochondral and fibroblastic lineages was studied through gene expression changes. Quantitative reverse transcription polymerase chain reaction (qRT-PCR) was used to determine the materials' ability to temporally modulate mRNA expression. This allowed for distinction of the various chondrocytic phenotypes of endochondral ossification and articular cartilage formation. $5\times10^5$ MSCs were seeded onto F1+, F2+, or control material (F1−) in culture plates and maintained under the same medium and environmental conditions described above. F1− was identical to F1+ with the exception of sterile water replacing hCPR, accounting for 100% of the gel liquid component. Cell pellets from each material (n=2) were collected as described above after five hours, one, three, seven, and fourteen days in culture. MSC pellets (n=2) containing $5\times10^5$ cells were retained at time zero to serve as the undifferentiated control gene expression. Pellets were stored at −80° C. until time of analysis. SABIOSCIENCES (Germantown, Md.) and QIAGEN (Germantown, Md.) reagents were used per manufactures' instructions to perform qRT-PCR. RNA was isolated from cell pellets using the RNEASY MINI KIT (Qiagen Germantown, Md.). Typically, recovered RNA was subjected to a second pass over new spin columns to remove PCR-interfering contaminants, which were likely alginate and/or calcium ions per conversations with the manufacturer. On-column degradation of DNA was conducted during the first pass using the RNASE-FREE DNASE SET (Qiagen Germantown, Md.).

Reverse transcription was performed with the $RT^2$ FIRST SRAND cDNA KIT (SABiosciences Germantown, Md.) on a MASTERCYCLER EP GRADIENT (Eppendorf; Hamburg, Del.) thermal cycler. Real-time (quantitative) PCR was performed in custom built primer plates (SABiosciences Germantown, Md.)) with SYBR GREEN MASTER MIX (SABiosciences Germantown, Md.)) on an ICYCLER iQ REAL TIME PCR detection system (Bio-Rad; Hercules, Calif.) to determine cycle threshold (Ct) values. Gene expressions of interest are listed in Table 2. Additionally, each sample was subjected to genomic DNA contamination, reverse transcription, and polymerase chain reaction control reactions on the custom built plates. Ct values greater than thirty-five were taken as "no call".

Proliferation data were analyzed with JMP STATISTICAL DISCOVERY SOFTWARE (SAS Institute; Cary, N.C.).

DNA values were subjected to a full factorial two-way analysis of variance ($\alpha$=0.05) to detect effects of culture substrate, time in culture, and their interaction. Post-hoc analyses using Tukey's HSD method ($\alpha$=0.05) were performed to identify differences between factor levels. Fold change in gene expression was calculated using the delta delta Ct ($\Delta\Delta$Ct) method, where $\beta$-actin served as the housekeeping (reference) gene for normalization and time zero MSCs served as the control group. Delta Ct ($\Delta$Ct) values were subjected to statistical analysis with SAS® Software (SAS Institute; Cary, N.C.) using linear mixed-effects models through the PROC MIXED procedure and Minimum Variance Quadratic Unbiased Estimation (MIVQUE0 option). Weight percent alginate and presence of hCPR were taken as fixed effects and time in culture was taken as a random effect. Interaction terms were not considered. Significant fixed effects were detected using Type III Sums of Squares F-tests ($\alpha$=0.05) with Satterthwaite approximations for denominator degrees of freedom and further subjected to Tukey's HSD post-hoc tests ($\alpha$=0.05) to detect differences among the factor levels. Significance of the random variable was detected using the Wald Z-tests ($\alpha$=0.05) on the variance parameter estimates on the diagonal of the covariance matrices (COVTEST option); p-values were taken as half of that reported due to testing at the boundary condition (variance equal to zero).

Figure 2:
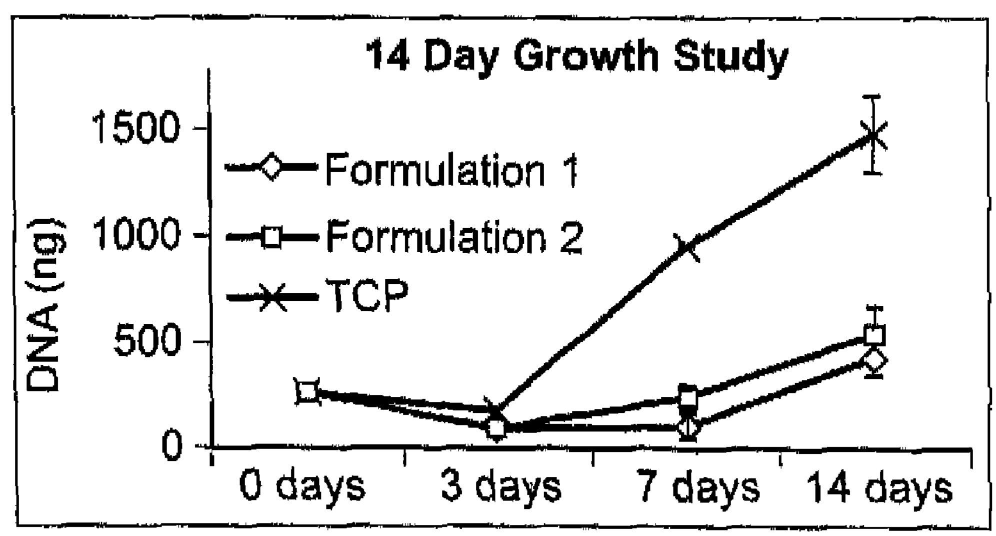
FIG. 2 shows rat mesenchymal stem cell (MCS) proliferation on and around 1 ml gels and in monolayer on tissue culture plastic (TCP). Day 0 represents $5\times10^4$ cells at time of seeding.
Figure 3F:
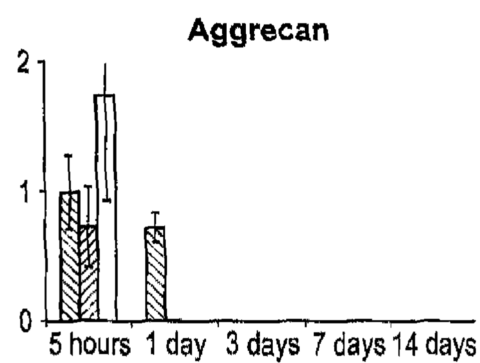
Figure 3G:
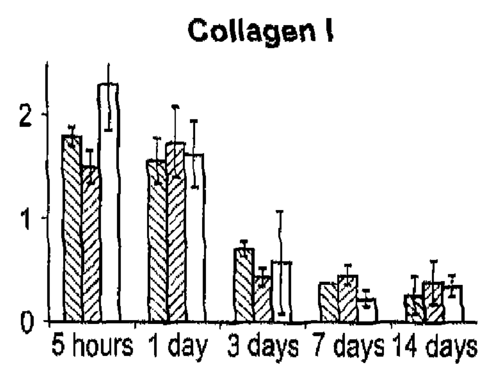
Figure 3H:
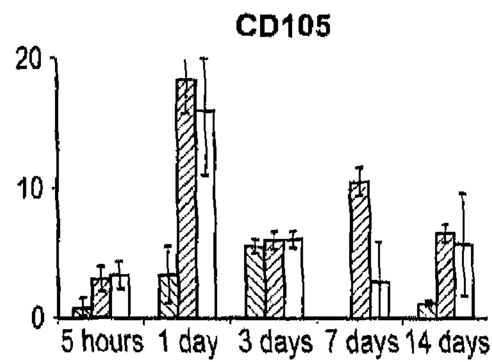
Figure 3I:
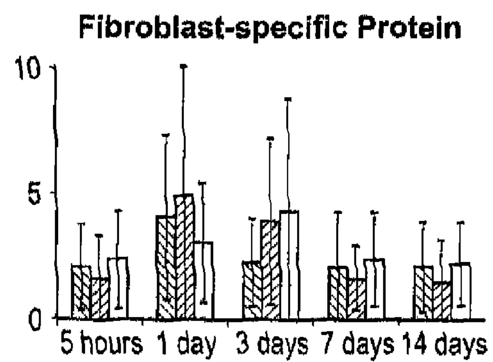

Now referring to FIG. 2. reduced proliferation rate is apparent in the presence of the gels in comparison to monolayer expansion on tissue culture plastic (TCP). A reduced proliferation rate as seen in the presence of the biomaterials is consistent with mesenchymal stem cell differentiation into nonhypertrophic chondrocytes. Data show groups averages (n=3) and =/− one standard deviation.

$5\times10^4$ second passage rat mesenchymal stem cells were seeded onto 1 ml samples of the experimental materials or onto tissue culture plastic (TCP). Cultures were maintained for the various time points shown. DNA was quantified in lysates using a commercial kit which employed fluorescent dye binding. All groups exhibited an initial small loss in viability by day three (p=0.0002) but group averages continued to rise thereafter. The proliferation rates on the concentrated platelet releasate-containing alginate/calcium phosphate composite materials were similarly reduced (p=0.1082) in comparison to the positive control monolayer culture on the tissue culture plastic (p<0.0001). This continued proliferation is consistent with gene expression results suggesting cells displayed a proliferative nonhypertrophic chondrocyte-like phenotype.

The MSC growth example demonstrated material cytocompatibility through maintained viability early after exposure to the material and biocompatibility through proliferative behavior later in the example (FIG. 2). Growth patterns associated with both experimental formulations and positive control TCP demonstrated very similar patterns, drop after seeding followed by rising, with material presences hindering the expansion rates. Significant effects of both the time in culture and culture substrate main factors and their interaction (p<0.0001 for all) were detected in the model (p<0.0001). Initially, average DNA values declined after seeding when compared to day three (p=0.0002), but after the day three time point all groups significantly increased throughout the example. Sequential levels of time in culture (differences between days three and seven; differences between day seven and fourteen) revealed highly significant increases in DNA quantities (p<0.0001 for both). Post-hoc testing of the interaction levels among culture substrates and times further clarified the materials roles in altered proliferation rates. Cells on tissue culture plastic (TCP) were the only group to demonstrate a significant interaction effect between days three and seven; differences between time points within the two experimental material cultures where not detected until the later day seven to fourteen comparisons (p<0.01 for both). MSCs cultured on the experimental formulation materials demonstrated a partially suppressed proliferation rate, as positive control tissue culture plastic (TCP) DNA values were significantly greater than experimental values at each time point after three days in culture. No statistical difference was detected between the experimental formulation groups at any given time point.

Now referring to FIG. 3, the data shows the fold changes in mRNA expression which are collectively suggestive of mesenchymal stem cell differentiation along an osteochondral pathway, specifically, to immature nonhypertrophic chondrocytes; average fold change (n=2) and +/− one standard deviation as compared to second passage monolayer rat mesenchymal stem cells are shown. Results from the studied genes of interest are shown in the bar graphs; collagen II and osterix mRNA results are not shown as their expression was absent. $5\times10^5$ second passage rat mesenchymal stem cells were seeded onto 1 ml samples of the experimental materials (F1+ and F2+) or onto a control material (F1−) similar to F1+ with water replacing the concentrated platelet releasate portion. Cultures were maintained for the various time points shown.

A quick burst of Runx2 expression followed by upregulation of Sox9 mRNA is consistent with early endochondral bone formation processes where mesenchymal stem cells take on the nonhypertrophic chondrocyte phenotype. Maintaining the expression of Sox9 as is seen in F2+ cultures in the absence of later hypertrophic chondrocyte, articular chondrocyte, and osteoblast markers (indicated in Table 2) indicate that cells are retaining this immature phenotype. Interestingly, mesenchymal stem cell markers were upregulated throughout the example due to the materials themselves but to a lesser degree from the suspected faster growth factor eluting F1+ group. Both the experimental materials containing hCPR (F1+ and F2+) and the control material without hCPR (F1−) demonstrated the ability to alter the gene expressions of second passage MSCs in comparison to time zero undifferentiated monolayer tissue culture plastic (TCP) reference cultures (fold change equal to unity).

Relative mRNA levels of the master transcriptions factors of osteochondrogenesis Sox9, Runx2, and osterix were examined in Example 1. Sox9 expression increased in each material group over the first three days of culture. F2+ specimens demonstrated a dramatic 175 average fold increase on day three and heavily contributed to observed significant effect of alginate weight percent in the formal analysis (p=0.022 factor level; p=0.026 post-hoc difference between 8 and 0 weight percent). Remaining above reference MSC levels of Sox9 mRNA, F2+ and F1− values declined after the day three peak; whereas the F1+ group demonstrated an absence of Sox9 expression on days seven and fourteen. Runx2 expression for F1+ and F2+ cultures increased over MSCs and peaked at day one and five hours, respectively; it was undetectable in cells cultured on the F1− control material throughout the example and in experimental materials after peaking. In contrast to Sox9 findings, F1+ material demonstrated a superior ability to induce Runx2 mRNA expression at 8.3 average fold increase. Osterix expression was only detected in one of the two MSC reference samples at the high Ct (low quantity) value of 32.7 and was "no call" for all other sample reactions (data not shown). Given the limited number of observations in the Runx2 and osterix models, n=7 and 1, respectively, statistical analysis of these data were uneventful in the fact that no significant effects were detected with such a limited population.

Both phenotype-specific and more generalized osteochondral protein encoded mRNAs were followed over the fourteen days. Osteoblastogenesis was assessed through osteonectin and osteocalcin gene expression. Osteocalcin expression was upregulated in experimental material cultures with that of F2+ showing the greatest average fold increase of 7.7; it was not detected after the five hour time point in these groups or at any time point for the F1− control group, resulting in a lack of observations for meaningful statistical analysis. Osteonectin gene expression was found throughout the experiment for all groups but was upregulated in the F2+ and more so in the F1− groups but only at day one. Measurements were suggestive of a loss with time ($p=0.058$) as seen after day one in all groups, and the presence of hCPR was found to inhibit osteonectin gene expression ($p=0.0003$). The more generalized osteochondral mRNAs for alkaline phosphatase, collagen 1, and aggrecan proteins were pursued. Collagen I was upregulated on average between 1.5 and 2.0 fold over MSCs at five hours and day one; after which, expression declined to below the fold change equal to unity reference value, accounting for an observed significant loss with time in culture ($p=0.043$). Alkaline phosphatase expression was highly variable at the five hour and day one time point for all (F1+, F2+, and F1−) and experimental (F1+ and F2+) materials, respectively. Complete inhibition of alkaline phosphatase expression was seen after 5 hours for F1− control material but persisted out to the day one time point for experimental hCPR containing materials. Aggrecan gene expression may have been upregulated in the F1− material group at five hours in culture but was suppressed in all groups after day one.

Additionally, the MSC-related surface integrin endoglin (CD105), fibrogenic protein S100a4 (fibroblast-specific protein (FSP)), and glyceraldehyde 3-phosphate dehydrogenase (GAPDH) mRNA expressions were monitored. Interestingly, CD105 mRNA was found to be significantly upregulated by the presence of hCPR ($p<0.0001$), and no effect was found in the FSP gene expression model.

TABLE 2

Summary of PCR reactions applied to cDNA from each specimen.

| Gene Symbol | Alias | Refseq # | Official Full Name |
|---|---|---|---|
| Runx2 | Cbfa1 | XM_346016 | Runt related transcription factor 2 |
| Sparc | — | NM_012656 | Secreted protein, acidic, cysteine-rich (osteonectin) |
| Sp7 | Osx | NM_181374 | Sp7 transcription factor |
| Alpl | Akp2/MGC93545/PHOA | NM_013059 | Alkaline phosphatase, liver/bone/kidney |
| Bglap | Bglap2/Bgp/Bgpr/Bgpra | NM_013414 | Bone gamma-carboxyglutamate (gla) protein |
| Col2a1 | CG2A1A/COLLII | NM_012929 | Collagen, type II, alpha 1 |
| Col1a1 | COLIA1 | XM_213440 | Collagen, type I, alpha 1 |
| Acan | Agc/Agc1 | NM_022190 | Aggrecan |
| Eng | MGC124909 | NM_001010968 | Endoglin |
| Sox9 | — | XM_343981 | SRY-box containing gene 9 |
| S100a4 | 18A2/42A/CAPL/MTS1/P9ka/PEL98/RNP9KA | NM_012618 | S100 calcium-binding protein A4 |
| Actb | Actx | NM_031144 | Actin, β- |
| Gapdh | Gapd | NM_017008 | Glyceraldehyde-3-phosphate dehydrogenase |
| RGDC | RGDC | U26919 | Rat Genomic DNA Contamination |
| RTC | RTC | SA_00104 | Reverse Transcription Control |
| PPC | PPC | SA_00103 | Positive PCR Control |

Proliferation data was analyzed with JMP® Statistical Discovery Software (SAS Institute; Cary, N.C.). DNA values were subjected to a full factorial two-way analysis of variance ($\alpha=0.05$) to detect effects of culture substrate, time in culture, and their interaction. Post-hoc analyses using Tukey's HSD method ($\alpha=0.05$) were performed to identify differences between factor levels.

Fold change in gene expressions was calculated using the delta delta Ct ($\Delta\Delta$Ct) method, where β-actin served as the housekeeping gene for normalization and time zero MSCs served as the reference group (fold change equal to unity). Delta Ct ($\Delta$Ct) values were subjected to statistical analyzed with SAS® Software (SAS Institute; Cary, N.C.) using linear mixed-effects models through the PROC MIXED procedure and Minimum Variance Quadratic Unbiased Estimation (MIVQUE0 option). Weight percent alginate and presence of hCPR were taken as fixed effects and time in culture was taken as a random effect. Interaction terms were not considered. Significant fixed effects were detected using Type III Sums of Squares F-tests ($\alpha=0.05$) with Satterthwaite approximations for denominator degrees of freedom and further subjected to Tukey's HSD post-hoc tests ($\alpha=0.05$) to detect differences among the factor levels. Significance of the random variable was detected using the Wald Z-tests ($\alpha=0.05$) on variance parameter estimates (COVTEST option); p-values were taken as half of that reported due to testing at the boundary condition (variance equal to zero).

TABLE 3

Reduced Data from the Proliferation Example

| Day | Condition | Specimen | DNA (ng) | Avg DNA (ng) | St Dev (ng) |
|---|---|---|---|---|---|
| 0 days | TCP | 1 | 269 | 259 | 9 |
| | | 2 | 251 | | |
| | | 3 | 257 | | |
| | Composition 1 | 1 | 244 | 240 | 5 |
| | | 2 | 242 | | |
| | | 3 | 235 | | |
| | Composition 2 | 1 | 254 | 257 | 10 |
| | | 2 | 269 | | |
| | | 3 | 249 | | |
| 3 days | TCP | 1 | 148 | 171 | 21 |
| | | 2 | 176 | | |
| | | 3 | 188 | | |
| | Composition 1 | 1 | 55 | 78 | 20 |
| | | 2 | 84 | | |
| | | 3 | 95 | | |
| | Composition 2 | 1 | 56 | 82 | 28 |
| | | 2 | 78 | | |
| | | 3 | 112 | | |
| 7 days | TCP | 1 | 956 | 960 | 9 |
| | | 2 | 954 | | |
| | | 3 | 971 | | |
| | Composition 1 | 1 | 87 | 101 | 61 |
| | | 2 | 168 | | |
| | | 3 | 49 | | |

TABLE 3-continued

Reduced Data from the Proliferation Example

| Day | Condition | Specimen | DNA (ng) | Avg DNA (ng) | St Dev (ng) |
|---|---|---|---|---|---|
| | Composition 2 | 1 | 186 | 234 | 51 |
| | | 2 | 227 | | |
| | | 3 | 288 | | |
| 14 days | TCP | 1 | 1274 | 1471 | 183 |
| | | 2 | 1636 | | |
| | | 3 | 1504 | | |
| | Composition 1 | 1 | 541 | 434 | 94 |
| | | 2 | 396 | | |
| | | 3 | 365 | | |
| | Composition 2 | 1 | 519 | 540 | 130 |
| | | 2 | 680 | | |
| | | 3 | 422 | | |

Example 2

Table 1 details the biomaterial composite formulations and preparation of the formulations F1+ and F2+ which were created through syringe mixing. A syringe containing sodium alginate (Sigma; St. Louis, Mo.) solution at twice the final concentration was coupled to a second containing 125-150 μm β-tricalcium phosphate (β-TCP) granules (Plasma Biotal, Ltd.; Derbyshire, United Kingdom), calcium sulfate dihydrate (USG Corp.; Chicago, Ill.), human concentrated platelet releasate (hCPR), and, for F2+, sodium citrate (Fisher; Waltham, Mass.). Components were mixed by twenty passes between the coupled syringes, which also initiated an ionic polymerization setting reaction. This mixture can be easily delivered through injection via a 16-gauge hypodermic needle prior to curing. Additionally, material controls with deionized water replacing hCPR were created and designated as F1− and F2−. hCPR was prepared under an Institutional Review Board-approved protocol at the University of Memphis (approval IRB #/date: H11-16/Sep. 9, 2010) through methodology adapted from White and Jennings. McCanless J D, Jennings L K, Cole J A, Bumgardner J D, Haggard W O. In vitro differentiation and biocompatibility of mesenchymal stem cells on a novel platelet releasate-containing injectable composite. J Biomed Mater Res A. 2012; 100(1):220-9 hereby specially incorporated by reference.

Processing was conducted at room temperature unless noted differently. ~120 ml of blood was acquired by venipuncture into 30 cc syringes and transferred to 50 ml conical polypropylene tubes containing citrate buffer. Plasma and buffy coat supernatants were collected after centrifugation (600 g). Platelets were then concentrated in plasma through further centrifugation (2,000 g), removal of the upper cell-free plasma (80% volume reduction), and resuspension into the remaining plasma. Platelet-rich plasma (PRP) was pooled (n=5), and clotted with 10% (wt/v) calcium chloride (50 μl/ml of PRP). Clotting occurred for one hour at 37° C. hCPR was expelled from the clot, sterile filtered (0.20 μm), and stored at −80° C. Specimens for this work were created using sterile materials. Alginate solutions were autoclaved. Calcium salts were gamma irradiated. Sodium citrate, hCPR, and deionized water (for F1− and F2− formulas) were sterile filtered; sterile sodium citrate solutions were lyophilized in syringes equipped with 0.20 μm syringe filters to obtain a sterile solid. Test specimens were created with ~3 ml mixes which were allowed to cure within 3 cc syringes; after curing (~10 minutes), syringe injection ports were cut off and cylinders of the material were expelled and cut to size.

Platelet-Derived Growth Factor (−BB and −AB) (PDGF) Elution: Growth factor release was assessed through elution studies with PDGF sandwich enzyme-linked immunosorbent assays (ELISAs) (PeproTech; Rocky Hill, N.J.). Elution was conducted from 1.5 ml specimens into 0.1 wt % albumin in phosphate buffered saline (PBS) eluent at 37° C. (n=4). 1.5 ml samples were pulled from an initial 40 ml at 5 hours, 1, 2, 3, and 5 days. Additionally to monitor PDGF depletion, 400 μl of hCPR was added to 40 ml eluent and sampled at time zero, 5 hours, 1, 2, 3, and 5 days (n=3). PDGF concentrations were taken as the average of duplicate ELISA measurements. Material, specimen number, and time were taken as independent experimental variables.

Simple chemotaxis was assessed with the RAW 264.7 clone TIB-71 (ATCC; Manassas, Va.) monocyte/macrophage cell line (monocytes) using 24-well Transwell® plates with 3 μm pore polycarbonate inserts (Corning; Lowell, Mass.). Lower wells were loaded with Dulbecco's modified Eagle's medium (DMEM), $10^{-8}$ M n-formyl-methionyl-leucyl-phenylalanine (fMLP) in DMEM, or 48 hour eluates of F1+, F2+, F1−, and F2−. Eluates were produced with 1.5 ml material specimens in 5 ml of DMEM. CELL TRACKER ORANGE (Lonza; Basel, Switzerland) labeled monocytes (3 μM) were loaded into upper wells in DMEM ($10^5$ cells/insert), and migration was allowed to occur for 4 hours (n=2). Those cells which did not migrate were removed using a PBS dampened cotton swab, and those which had migrated were collected in the lower well through centrifugation (400 g, 15 minutes) of the plate with inserts installed. Cells in lower wells were then suspended via micropipette mixing and counted indirectly using fluorescence spectroscopy and a standard curve of monocytes which had been seeded at the start of the experiment. Values were taken as the average of duplicates. Transendothelial migration was assessed using a very similar methods as described above with 8 μm inserts (n=2); all differences are noted in the following. Lower surfaces of inserts had been coated with bovine collagen type I (50 μg/ml for 1 hour), and upper surface was coated with 50 μl of 50 μg/ml growth factor-reduced MATRIGEL (BD Biosciences; Franklin Lakes, N.J.). A confluent endothelial monolayer was established on upper insert surfaces using third passage primary human umbilical vein endothelial cells (HUVECs) (ATCC, Manassas, Va.). $10^4$ HUVECs were seeded on the upper insert surface and allowed to expand for five days in bovine brain extract endothelial cell growth kit (BBE) (ATCC)-supplemented M200 (Invitrogen; Carlsbad, Calif.) with daily medium changes.

Simple chemotaxis of HUVECs was assessed on upper and lower surface collagen-coated 8 μm inserts. Lower wells contained M200, BBE-supplemented M200, or DMEM material eluates. HUVECs were starved overnight in 0.5 vol % fetal bovine serum (FBS)-supplemented M200 and plated at $5\times10^4$ cells/insert in M200. Migration was allowed for 4 hours. After which, cells on the upper insert surfaces were removed with a PBS-dampened cotton swab, and those which had migrated to the lower surface were cold shocked with 0° C. PBS and fixed with −20° C. methanol on ice. Fixed cells were labeled with 10 μM ethidium homodimer-1 (EthD-1) (Invitrogen) in PBS and imaged using fluorescence microscopy. Four frames of view (100×) per insert were captured and cells counted using FIJI/ImageJ software (NIH; Bethesda, N.J.). The experiment was repeated to confirm trends in the results.

Enzymatic HUVEC invasion was performed in 8 μm inserts through 50 μl of MATRIGEL (BD Biosciences; Franklin Lakes, N.J.) diluted 1:3 with M200. Cells were starved overnight, plated at $1.5\times10^5$ cells/insert in M200, and allowed 30 hours to migrate to the lower surface. Experimental groups, fixation processing, staining, and image acquisition was identical to that described above for the simple chemotaxis assay. Image analysis was again performed with FIJI/ImageJ software using 100× fluorescent micrographs, but total cell area ($\mu m^2$) was used as opposed to raw cell counts.

The ability of materials to induce HUVEC tube formation on Matrigel blends was studied. M200, BBE-supplemented M200, or using DMEM material eluates were mixed with MATRIGEL at 2:1 volume ratios. 65 μl of blends were put in 96-well plates (n=3). $5\times10^4$ second passage HUVECs were seeded on gel surfaces. Tube formation was assessed using digital 40× micrographs of the cultures 12 hours after seeding. FIJI/ImageJ software was used to analysis tube formations; total tube length (μm), number of tubes, and number of junctions were determined.

Statistical analysis of all data was performed using SAS software (Cary, N.C.). ANOVA ($\alpha$=0.05) was used for main factor(s) effect tests in ELISA and motility data. Tube formation data was subjected to MANOVA with Wilks' $\nabla$ test statistic ($\alpha$=0.05) to detect main factor effects and canonical correlation analysis to assess the existence of relationships among the dependent variables. Tukey HSD post-hoc analyses ($\alpha$=0.05) were conducted in the event that main factor effects were detected.

Figure 4:
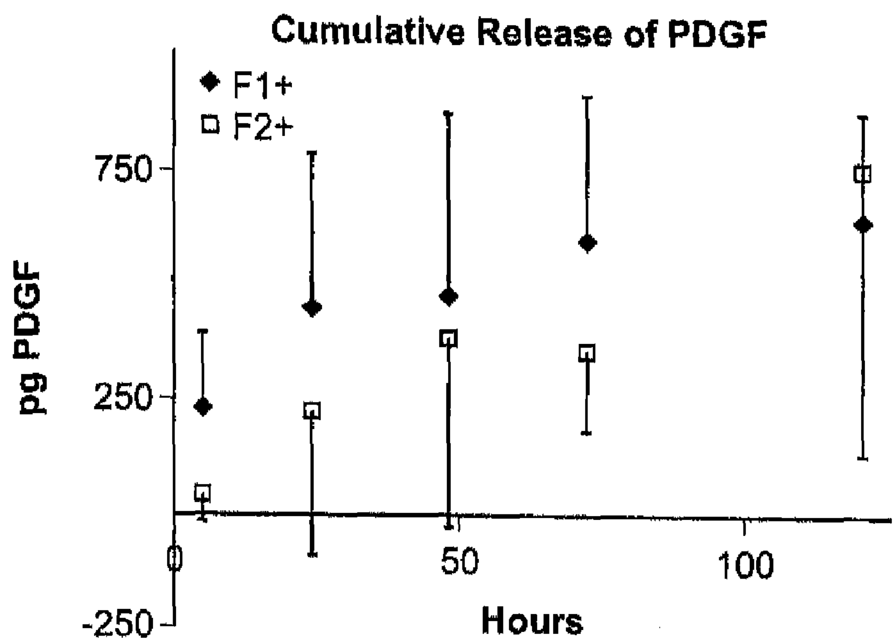
FIG. 4 shows cumulative release of Platelet-derived growth factor (PDGF) as it diffused from F1+ and F2+. Platelet-derived growth factor (–BB and –AB) release from F1+ and F2+ was tracked for each specimen individually (n=4) at 5, 24, 48, 72, and 120 hours. Concentration values were determined through ELISA.
Figure 5:
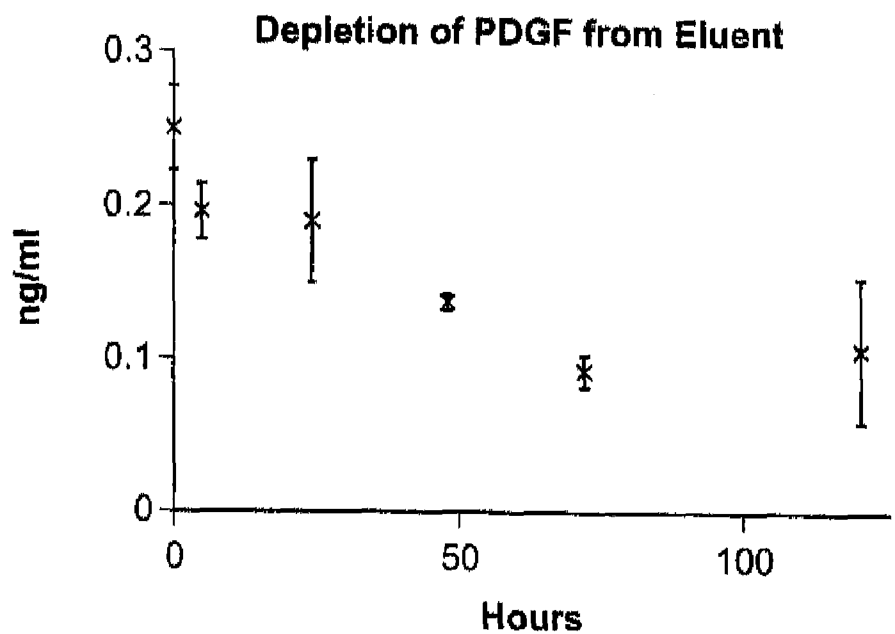
FIG. 5 shows depletion of PDGF from eluent. Loss of ELISA-detectable PDGF within the experimental setup was monitored through the addition of 400 μL hCPR to 40-mL eluent and sampled at time zero, 5 h, 1, 2, 3, and 5 days (n=3). The system demonstrated a consistent depletion of PDGF out to 72 hours; this loss with time was found significant ($p<0.0001$). At 120 hours an average 65% of the initial PDGF was undetectable. Data are shown as average values with error bars indicated plus/minus one standard deviation.

Now referring to FIGS. 4 & 5, PDGF was observed to accumulate within eluents as it diffused from F1+ and F2+; depletion of PDGF in the experimental setup was monitored separately, through spiking eluents with hCPR. Both accumulation and depletion were monitored over a five day period. Based on 5 and 24 hour data, F1+ appears to release growth factors at an accelerated rate compared to F2+; this observation is in-line with F1+ having a lower weight percentage of alginate compared to F2+, corresponding to a lower diffusion coefficient. Significant differences were found when individual specimen profiles were considered (p=0.0027) and support F1+'s accelerated release rate with two F2+ specimens eluting significantly less PDGF than one F1+ specimen. Average values are indicated by markers with plus and minus one standard deviation error bars shown for F1+ and F2+, respectively.

Early release values (5, 24, and 48 hours); suggest a more sustained release from F2+, the formula containing a higher weight percentage of alginate, as compared to F1+. Without temporal consideration, no significant difference was detected between the materials, but alternatively, values were found to increase with time (p=0.0033). Additionally and with some insinuation about F2+ having a slower release rate, variance among specimens was found significant (p=0.0027). Independent post-hoc grouping of specimen and time factors showed two F2+ specimens released significantly less PDGF than one F1+ specimen and 5 hour PDGF accumulation was significantly lower than that at 120 hours, respectively.

Now referring to FIG. 5 the depletion experiment showed a loss of PDGF with time (p<0.0001) which was indistinguishable between specimens. The average concentration of the spiked eluents had depleted 65% by 120 hours.

Now referring to FIGS. 6A & 6B, monocytes demonstrated inflammatory-related chemoattractant properties of eluates from both experimental and material control specimens. 74% and 83% of seeded monocytes had migrated to the lower wells containing F1+ and F2+ eluates in the simple migration assay, respectively. FIG. 6A shows monocytes demonstrated inflammatory-related chemoattractant properties of eluates from both experimental and material control speciments. RAW 264.7 clone TIB-71 mouse monocyte migration assays results are shown. F1+, F2+, F1− and F2− groups indicate the use of material eluates. n-formyl-methionyl-leucyl-phenylalanine (fMLP) was used as a positive chemotactic control at $10^{-5}$ M unsuccessfully, and Dulbecco's modified Eagle's medium (DMEM) was used as a negative control. $10^5$ monocytes were placed in the upper inserts of TRANSWELLS (Costar, Cambridge, Mass.). and allowed to migrate towards experimental and control solutions in the lower well.

Both assays (FIGS. 6A and 6B) demonstrate the inherent nature of the alginate/β-tricalcium phosphate raw materials to induce some monocyte activation (F1− and F2−) with enhanced ability being shown for the experimental, human concentrated platelet releasate-containing materials (F1+ and F2+).

Now referring to FIG. 6B, eluates corresponding to material controls F1− and F2− also showed the ability to attract monocytes, although to the lesser extent, at 23% and 24% cell migration, respectively; these material control values were still a significant increase over the DMEM negative control ($p \leqq 0.03$). Fewer monocytes had migrated in the more demanding transendothelial migration assay where 54% and 67% of seeded cells had relocated to the lower wells for F1+ and F2+ eluates respectively. Nevertheless, F1− and F2− eluates were able to induce significantly more monocytes to transverse the HUVEC monolayer than the DMEM negative control ($p \leqq 0.004$). Unfortunately, the fMLP positive control did not demonstrate chemoattractant properties in either assay at the low concentration tested ($10^{-8}$ M) and was undistinguishable from the DMEM negative control in post-hoc test results.

Now referring to FIGS. 7A & 7B, which shows results from the HUVEC motility assays that demonstrated the angiogenic-related chemoattractant qualities with these primary cells for both experimental and control material eluates. FIGS. 7A & 7B show angiogenic-related chemoattractant qualities from both experimental and control material eluates. Human umbilical vein endothelial cells (HUVECs) migration assays results are shown. F1+, F2+, F1−, and F2− groups indicate the use of material eluates. M200 medium and bovine brain extract kit-supplemented M200 medium served as negative and positive controls, respectively. Both assays demonstrate the inherent nature of the alginate/β-tricalcium phosphate raw materials to induce some HUVEC activation (F1− and F2−) with enhanced ability being shown for the experimental, human concentrated platelet releasate-containing materials being evident for F2+ only in the invasion assay (FIG. 7B) and F1+ demonstrating this enhancement in both assays.

Experimental F1+ material eluate clearly induced a significant increase in HUVEC migration over all other groups in the simple migration assay ($p \leqq 0.0001$). Whereas, experimental F2+ material eluate and positive control BBE-supplemented M200 values only approached significant increases over the negative control M200 in this assay (p=0.0616 and 0.0672, respectively). Although to a lesser degree than its hCPR-containing experimental counterpart eluate, F1− eluate was able to induced simple HUVEC migration over the M200 negative control (p=0.0455). Haptotactic activities of HUVECs in the invasion assay were much more evident of effects and differences. The ability to induce a strong enzymatic-driven invasion from HUVECs was apparent with the 30-fold increase over M200 alone due to BBE-supplementation in negative and positive controls (p<0.0001); significant increases above the negative control were seen for all other groups ($p \leqq 0.0003$). F1+ and F2+ eluates individually induced greater endothelial invasion than their control material counterparts F1− and F2− (p=0.0024 and 0.0033, respectively). Additionally, F2+ eluate suggested the greatest chemoattractant ability for these cells, being the only group to significantly exceed the positive control with an average 52% increase in lower insert surface cell coverage area (p=0.0038) which also corresponded to an average 22% increase over F1+ eluate values.

Referring to FIG. 8, in vitro angiogenesis was further assessed through the ability and extent of spontaneous tube formation by HUVECs. Qualitatively, micrographs of experimental material eluates from F1+ and F2+ produced more uniform cell organization networks. Organizations within the experimental groups demonstrated wider, continuous branches, and less cell compaction at junction points, while other groups demonstrated smaller branches with greater width variability and multiple branches which terminated on the substrate as opposed to continuity between two junction points. MANOVA of image analysis results for total tube length, tube count, and junction count demonstrated a Wilks' ∇=0.081 (p=0.0098) with the large majority of accountable variance within the model stemming from the effect of MATRIGEL (BD Biosciences; Franklin Lakes, N.J.) blend type on total tube length; blend type did not demonstrate significance in tube and junction count variance. However, and as expected, from the nature of such branching network systems, tube and junction count were predictive of one another, producing high canonical correlation (0.9726). Reflecting back on length measures, F1+ eluate, and to a lesser degree, F2+ eluate demonstrated superiority in total length measures over their non-hCPR containing counterparts with 255% and 220% increases (p=0.0024 and 0.0192, respectively).

Figure 8A:
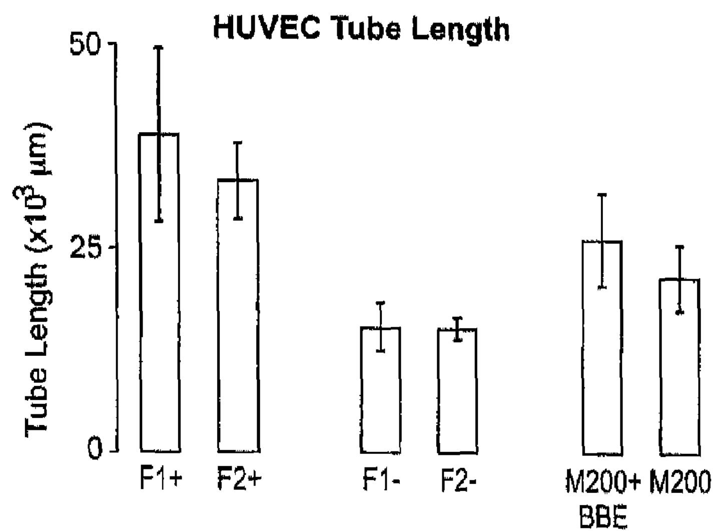
FIG. 8A shows in vitro angiogenesis assessed through the ability and extent of spontaneous tube formation by HUVECs.

Human umbilical vein endothelial cells (HUVECs) spontaneous tube formation assay on Matrigel (basement membrane gel) blends with test solutions was studied. F1+, F2+, F1−, and F2− groups indicate the use of material eluates in DMEM. M200 (Invitrogen; Carlsbad, Calif.) medium and bovine brain extract kit-supplemented M200 medium served as negative and positive controls, respectively. Test solutions were mixed with Matrigel at 2:1 ratio, and 65 ul of the blends were allowed to cure in 96-well plates (n=3). 5×10^4 second passage HUVECs were seeded on gel surfaces. Tube formation was assessed using digital 40× micrographs of the cultures 12 hours after seeding. FIJI/ImageJ software was used to analysis tube formations; total tube length (μm), number of tubes, and number of junctions were determined. Images were captured after 12 hours. IMAGEJ (NIH; Bethesda, N.J.) software was used to determine total branch length, branch count, and junction count, shown in FIGS. 8A-8C as average values with bars showing plus/minus one standard deviation. Multivariate analysis determined the eluate/media test factor to have a significant effect on tube length (p=0.0098). FIG. 8A shows the results from the total branch length analysis and demonstrates increased total branch length from F1+ and F2+ elates in comparison to their counterparts which did not contain human concentrated platelet releasate (p=0.0024 and 0.0192, respectively).

Figure 8B:
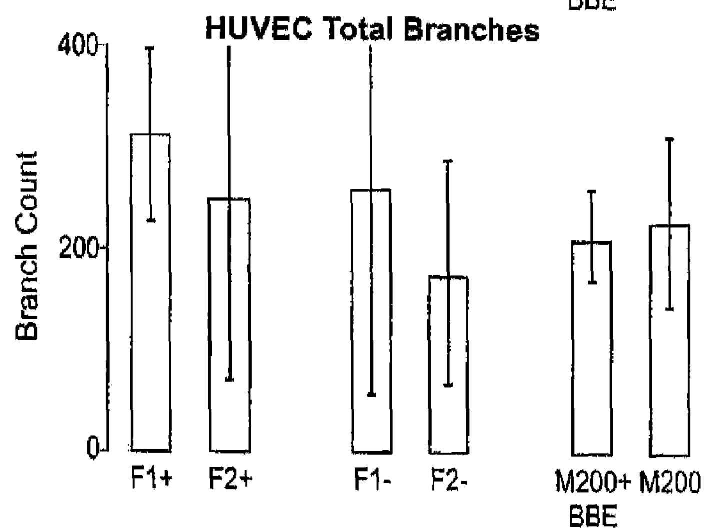
FIG. 8B shows in vitro angiogenesis assessed through the ability and extent of spontaneous tube formation by HUVECs.
Figure 8C:
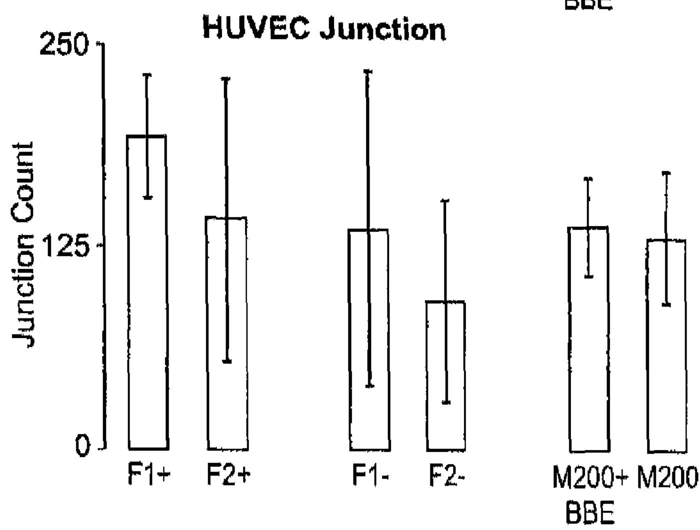
FIG. 8C shows in vitro angiogenesis assessed through the ability and extent of spontaneous tube formation by HUVECs.

FIGS. 8B & 8C show the results from total branch count and total junction count measures, respectively; neither variable was found to be effected as a result of eluate/media type. Example 2 shows the in vitro the capability of the biomaterial composite composites to induce motility in both a monocyte cell line and primary immature endothelial cells, conjugated motility of monocytes through a confluent monolayer of endothelial cells, modeled haptotactic-induced endothelial cell passage through basement membrane-derived gel, and observed spontaneous induction of endothelial cell tube formation all of which reflect on inflammatory and angiogenic responses. Collectively the current and prior findings of monocyte activation and osteochondrogenesis have confirmed the hCPR-containing alginate/β-TCP composites' ability to induce an in vitro response similar to that which occurs early within a fracture site and, more specifically, hematoma-initiated inflammation and angiogenic-type behaviors.

Figures 8D, 8E, 8F:
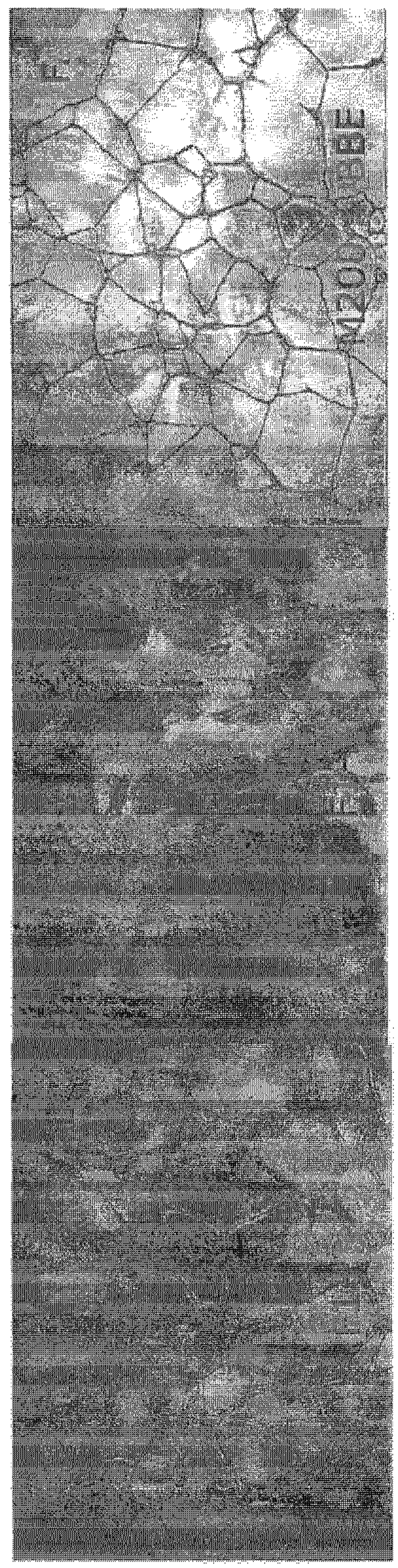
FIG. 8D shows D representative F1þ tube formations, which were similar to F2þ.
FIG. 8E: shows representative F1− tube formations, similar to F2− and M200 medium.
FIG. 8F shows BBE-supplemented M200 group with the ImageJ created overlay of the branch skeleton used to generate the raw branch and junction data.

In FIGS. 8D-E F1þ and F2þ groups consistently demonstrated a well-formed network of branches which terminated at junction points; this observation was similar to that see for M200 þ BBE. Branches for the experimental F1þ and F2 þ groups typically were thicker in diameter/width, qualitatively. F1−, F2−, and M200 groups, which did not contain growth factors, produced poorly formed networks and generally retracted into cell masses, seen in (E). On close inspection of (E), it is apparent that multiple, small branches that often terminated on the gel itself were seen protruding from individual junctions from the cell masses and explain why the number of branches and junctions were not found to be significantly affected by the various groups.

Healthy reformation of bone and vascularization adjacent to joints exhibiting early stages of degeneration provides a means of reversing or, inhibiting the advancement of the age-related disease (osteoarthritis) through addressing these detrimental bone changes. Incorporation of hCPR within F1+ and F2+ alginate-containing biomaterial composites allows for controlled release of autologous bioagents. The releasate supplemented the inherent material-induced initiation of monocyte and endothelial cell recruitment that is associated with the early occurrences of bone tissue remodeling and induced a well-organized endothelial tube networks. This treatment in a patient may lead to healthy osseous tissue regeneration and be associated with the delay or reversal of joint degeneration through rejuvenation of this underlying, unhealthy tissue.

Example 3

There exists a clinical need for consistent bone remodeling within problematic sites such as those of fracture nonunion, avascular necrosis, or irregular bone formations. To address such needs, a biomaterial composite composition is provided to induce early inflammatory responses after implantation and to provide later osteoconductive scaffolding for bone regeneration. Biomaterial composite-induced inflammation parallels the early stage of hematoma-induced fracture repair and allows scaffold-promoted remodeling of osseous tissue to a health state. Initiation of the wound healing cascade by two human concentrated platelet releasate-containing alginate/β-tricalcium phosphate biocomposites has been studies in vitro using the TIB-71™ RAW264.7 mouse monocyte cell line.

This in vitro example relates to tunable interactions between the platelet releasates and the biomaterial composites for enhancing hematoma-like fracture repair. Additionally, minimally invasive delivery for in situ curing the implant system via injection was demonstrated in rat tail vertebrae using micro computed tomography.

Two injectable alginate hydrogel/β-tricalcium phosphate granule composites containing bioactive concentrated human platelet releasate (hCPR), designated as F1+ and F2+, are described in Table 1 were prepared. The formulations are designed such that the alginate weights percentage and the β-tricalcium phosphate volume percentage is inversely related. An additional, non-biologic formulation designated F2− was created identical to F2+ with the exception of sterile deionized water replacing hCPR. The F2− formulation was selected for inclusion as a material control for the current example as opposed to an F1− formulation due to having a higher weight percent alginate which was anticipated to induce an increased inflammatory response due to higher levels of impurities associated with the higher alginate percentage. Ma P X. Alginate for Tissue Engineering. In: Ma P X, Elisseeff J, editors. Scaffolding in Tissue Engineering. Boca Raton, Fla.: CRC Press; 2006. p. 13-25.

hCPR was prepared under an Institutional Review Board-approved protocol at the University of Memphis (approval IRB #/date: H11-16/Sep. 9, 2010) through methodology adapted from White and Jennings. White M M, Jennings L K. Appendix. Platelet Protocols: Research and Clinical Laboratory Procedures. San Diego: Academic Press; 1999. p. 99-101, hereby specially incorporated by reference. All steps were performed at room temperature unless otherwise stated. Whole blood (120 ml) was obtained by venipuncture from each of five informed, consenting graduate student participants into 30 cc syringes and gently mixed with citrate buffer in 50 ml conical polypropylene tubes. Plasma and buffy coat supernatants were collected after a ten minute low-speed centrifugation (600 g). Platelets were then concentrated in plasma by a fifteen minute higher speed centrifugation (2,000 g), removal of top acellular plasma (80% volume reduction), and resuspension into the residual plasma. Platelet-rich plasma (PRP) from all donors (n=4 or 5 per draw session) was pooled, and clotting was induced through the addition of 10% (wt/v) calcium chloride (50 μl/ml of PRP). Clot formation was allowed to proceed for one hour at 37° C. hCPR was expelled from the clot, sterile syringe filtered (0.20 μm), and stored at −80° C. until time of use.

The in vitro test specimens of the current example were made by placing 1.5 ml of sodium alginate (Sigma PIN 71238; St. Louis, Mo.) solution at twice the final weight percentage in a 3 cc syringe. A separate syringe containing 125-150 μm β-tricalcium phosphate granules (Plasma Biotal; Derbyshire, UK), the major setting reagent calcium sulfate dihydrate (as USG TERRA ALBA (United States Gypsum Company; Chicago, Ill.)), and 1.5 ml of hCPR (with or without USP grade sodium citrate (Mallinckrodt Baker Inc.; Phillipsburg, N.J.)) was then coupled to the alginate containing syringe, followed by mixing (~15 passes). Upon homogenizing, the material was positioned into one of the syringes and allowed to cure for a minimum of ten minutes. After curing, the ejection port of the syringe was removed, and composite expelled.

All in vitro specimens were prepared using sterile materials. Alginate solutions were autoclaved for twenty minutes under slow venting in 40 ml aliquots using 50 ml conical polypropylene tubes. Calcium salts were preloaded into syringes and exposed to low-dose gamma irradiation. Sodium citrate (for F2+ and F2−) was sterile filtered as a solution; required amounts were for each mix were filled into sterile 3 cc syringes with ~1.5 ml of headroom and fitted with a sterile syringe filter, frozen (−80° C.), and lyophilized in an upright position. Monocytes and nitric oxide in vitro assays: microscopy, Griess reagent, and qRT-PC In vitro temporal induction of an inflammatory response due to material exposure was assessed using the TIB-71 RAW264.7 cell line (ATCC; Manassas, Va.). Culture methods were based on those described by Nicolin et al. Nicolin V, Ponti C, Narducci P, Grill V, Bortul R, Zweyer M et al. Different levels of the neuronal nitric oxide synthase isoform modulate the rate of osteoclastic differentiation of TIB-71 and CRL-2278 RAW 264.7 murine cell clones. Anat Rec A Discov Mol Cell Evol Biol. 2005; 286(2):945-54. The transformed line was derived from an Abelson leukemia virus-induced tumor in the BALB/c strain and exhibits a monocyte/macrophage phenotype with receptor activator of nuclear factor kappa-β-ligand (RANKL)-induced osteoclast-like differentiation potential. All cultures were maintained in 10% (v/v) fetal bovine serum-(FBS-) supplemented high glucose Dulbecco's Modified Eagle's Medium (DMEM-HG) containing 100 IU/ml penicillin, 100 μg/ml streptomycin, and 2.5 μg/ml amphotericin B. Cells were expanded in T-flasks and passaged by scraping cells off the flask with a rubber policeman and replating at $4\times10^4$ cells/cm$^2$. Experimental cultures of $10^6$ cells were seeded onto 60 mm tissue culture plastic Petri dishes in 5 ml of medium and allowed to attach overnight. On the following day, Petri dishes were randomly assigned to one of five groups (n=9/group): 1) untreated, time zero basal condition; 2-4) exposure to 0.5 ml cylinders/dish of F1+, F2+, or F2− 5) 5 μg/ml lipopolysaccharide (LPS) (Simga P/N L4516) nitric oxide (NO) proinflammatory endotoxin control.

Nitric oxide (NO) production was assessed through media nitrite levels. Basal measurements were taken as time zero (n=9; group 1) and after 5, 24, and 48 hours of treatment exposure (n=3/group/time point; groups 2-5). Media nitrite levels were resolved using the GRIESS REAGENT SYSTEM (Promega Corp.; Madison, Wis.) per the manufacture's protocol. Individual sample values were taken as the average of duplicate measures. Upstream changes in inducible (type IP-nitric oxide synthase (iNOS) gene expression were determined on duplicates. mRNA was isolated from cells and subjected to qRT-PCR to investigate changes in the iNOS gene expression. Immediately after performing the Griess assay, media and materials were discarded from dishes, and monolayers were gently rinsed with phosphate-buffered saline (PBS) and scrapped into the rinse. For time zero measures, cells for each qRT-PRC sample condition (n=2) were obtained from the populations of four dishes by combining in a 15 ml conical tube, and for all other time points, samples (n=2 per condition) were obtained by splitting cells from one of the three replicates between the two conical tubes. Cell pellets were formed by centrifugation, and the supernatant was aspirated. Cells were then rinsed again through resuspending in PBS. Cells were then centrifuged, and the supernatant aspirated completely. Pellets were stored frozen (−80° C.) until time of analysis.

Upon collecting and freezing all groups, pellets were thawed and RNA was isolated using the RNEASY MINI KIT (Qiagen; Germantown, Md.) with on-column DNA digestion using RNASE-FREE DNASE SET (Qiagen). RNA (4.9 μg) was reverse transcribed into cDNA using the RT$^2$ FIRST STRAND KIT (Qiagen) on a MASTERCYCLER EP GRADIENT (Eppendorf; Hamburg, Del.) thermocycler. qPCR (25 μl) was then performed on an ICYCLER IQ (Bio-Rad; Hercules, Calif.) to determine threshold cycle ($C_T$) values using 1.5 μl of each cDNA sample using 1.5 μl of each (sense and anti-sense) 10 mM primer solution (Integrated DNA Technologies; Coralville, Iowa) (Table 2), 12.5 μl SYBR Green/Fluorescein qPCR MASTERMIX (Qiagen), and nuclease-free water. cDNA corresponding to one gene was amplified per well, and cDNA for iNOS and housekeeping genes ribosomal 18s (Rn18s) and β-actin mRNAs were amplified for all samples. Additionally, efficiency curves were created for each primer pair using the serial dilutions of a common cDNA sample.

Photomicrographs were acquired at 40×, 100×, and 200× for all groups and time points using an EVOS XL Microscope (AMG; Bothell, Wash.) to assess morphological changes. Changes in NO concentrations and iNOS expression as an effect of treatment group and time in culture were assessed using SAS SOFTWARE (SAS Institute; Cary, N.C.). NO concentrations were subjected to full factorial two-way ANOVA ($\alpha$=0.05) to detect factor significance using the proc glm procedure. Factor levels were further investigated for differences ($\alpha$=0.05) using Tukey HSD (main factors) and Tukey-Kramer (interaction factor) multiple comparison testing of the means and the least-squared means, respectively. QRT-PCR data were transformed prior to ANOVA. Efficiency curve data were used to determine the adjusted cycle threshold ($C_T$) values, and $\Delta C_T$ values were calculated taking Rn18s as a housekeeping gene. Lock E F, of al. Efficiency clustering for low-density microarrays and its application to QPCR. BMC Bioinformatics. 2010; 11:386. $\Delta C_T$ values were then linearized to proportions (relative to Rn18s) per standard $\Delta C_T$ methodology. Dummy variables ranging −1 to 1 were assigned to treatment groups such that differences in the average (Rn18s relative) proportion values were linearly reflected in the differences of the assigned values spanning the two unit range. Linearized proportion values were then used for modeling of the system; data were modeled as a second-order response surface, using the proc rsreg procedure in the SAS software, where time was taken as a quadratic and linear independent variable, treatment as an independent linear covariate, and the linearized proportions as the response (or dependent variable). Canonical analysis of the model was used to characterize the surface (stationary point and eigen values), and ANOVA ($\alpha$=0.05) for the developed model was used to detect significant effects of the factors.

Deliverability, cohesion, and localization of the F1+ injectable composite were assessed in Ca-2 and -3 rat caudal vertebrae. F1+ was chosen as the worst case formulation due having a higher weight percent of solids. Rat tails were harvested post mortem from animals enlisted in an unrelated Institutional Animal Care and Use Committee-approved example and stored in ethanol until time of use. A 4 cm opening was created along the tail in the anterior-posterior direction using a scalpel, penetrating skin and the underlying ligament. The soft tissue was spread to create access the vertebral bodies. Small openings were created in the cortical shells approximately 1.5 mm distal the vertebral endplates using a tooth burr and drill. A small amount of the F1+ material was delivered via injection through a 16-gauge needle. Using a micro computed tomography (μCT) 40 (Scanco USA, Inc.; Wayne, Pa.) and associated software 3D reconstitution, analysis of the vertebrae and implant locations were performed. An area containing only the implant was partitioned and the volume percent β-tricalcium phosphate and β-tricalcium phosphate granule degree of anisotropy (DA) was reported on using the software functions. Three implantations were performed and scanned, but only one site was partitioned out for the β-tricalcium phosphate granule analysis.

Cultures from all groups were composed of cells which typically exhibited a spherical morphology with the occasional occurrence of cell spreading/flattening onto the tissue culture plastic. F1+ and F2− groups demonstrated a relatively consistent morphology at all time points as only a small portion of the cells demonstrated spreading, and those spreading cells typically had a spindle-like shape. These round and spindle morphologies and population percentages were similar to the overnight-attached cells at time zero. After 48 hours the majority of cells still exhibited a spherical morphology, but cells in the F2+ and LPS groups, appeared larger. Occasional cells in F2+ and LPS cultures were irregular, flattened, and spread with more filopodia compared to the F1+ and F2− cultures and basal time zero condition.

Figure 9:
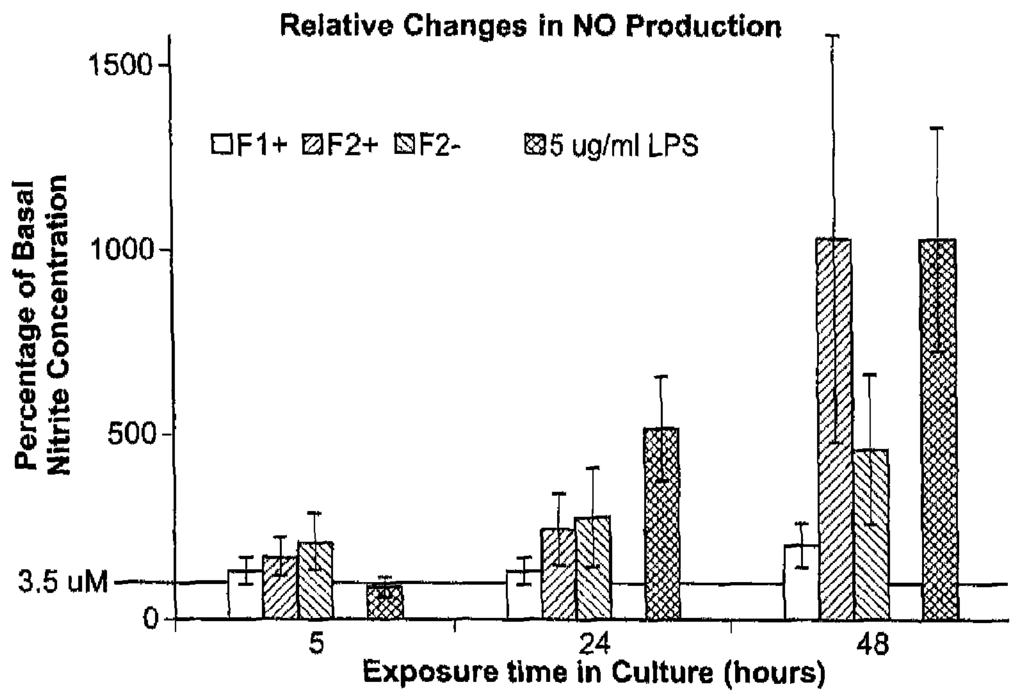
FIG. 9 shows data for NO production measures as nitrite accumulation in TIB-71 RAW264.7 mouse monocyte cell line cultures are shown relative to the basal time zero level of 3.5±0.9 μM nitrite and indicated in the figure at the 100% value. Columns show average percentages and bars indicate ± one standard deviation. Data were investigated through a full factorial two-way ANOVA and Tukey tests (a=0.05, for all).

Now referring to FIG. 9, measurements associated with NO production were normalized against the average basal level of nitrite at time zero (3.5±0.9 μM). The effects of treatment, time in culture, and interaction term were all found to significantly increase NO concentrations ($p<0.0001$ for all factors). Exposure to F2+, F2−, and LPS all induced a significant accumulation of NO by at least 48 hours of exposure ($p<0.0001$, 0.02, and 0.0001, respectively). Averages associated with F2+ and LPS treatments reached ten times that of the time zero basal level. Cultures exposed to LPS showed significant accumulation after only 24 hours of treatment ($p=0.0036$). Although cultures exposed to F1+ demonstrated an average accumulated nitrite level twice that of time zero at 48 hours, significant differences between F1+ levels and the basal time zero condition were not detected in any of the multiple comparisons analysis. Although F2− was significantly increased over that of the basal condition, no difference in accumulation was detected between it and the F1+ condition at any time point. The analysis suggested that the presence of hCPR bioagents in combination with lower weight percent alginate and/or higher volume percentages of TCP (F1+) maintained a basal NO production rate in monocytes in comparison to that seen associated with 5 μg/ml LPS endotoxin exposure (and F2+). Whereas, accumulation in the F2+ group (hCPR, higher weight percent alginate, and lower volume percentage of β-tricalcium phosphate reached levels comparable to that of LPS after 48 hours.

Figure 10:
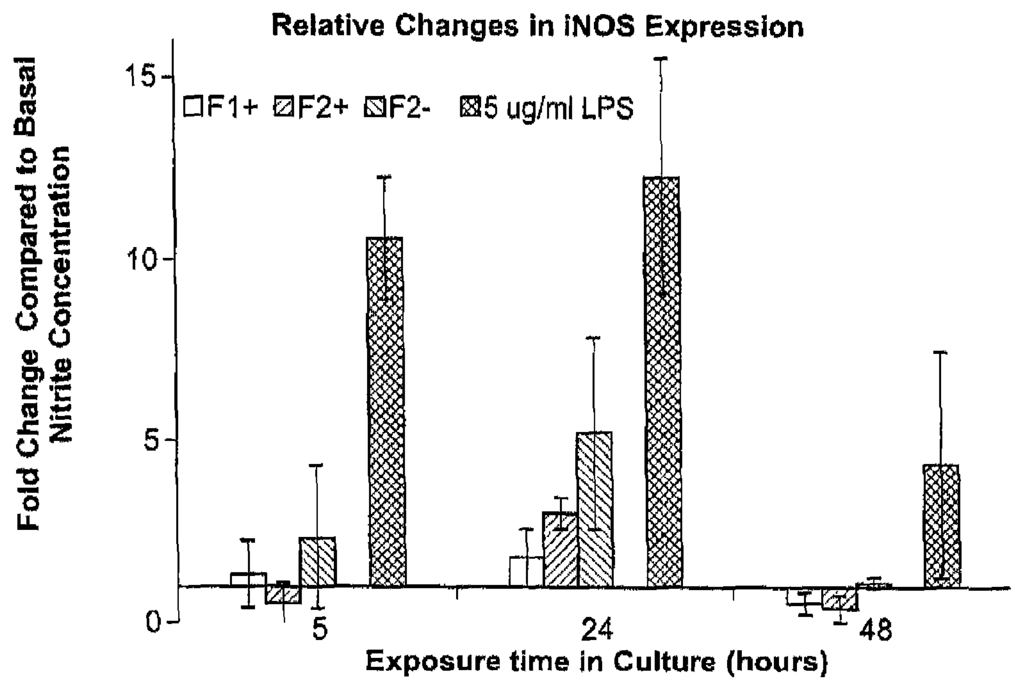
FIG. 10 shows reduced qRT-PCR data for the fold change iNOS expression in TIB-71 RAW264.7 mouse monocyte cell line cultures as a result of material or LPS endotoxin exposure over time is shown. Data reduction was performed using $\Delta\Delta C_T$ analysis (standard $\Delta\Delta C_T$ with the additional consideration primer pair efficiency). ANOVA ($\alpha$=0.05) was applied to a second-order response surface model in regards to time with treatment as a linear covariate on linearized $\Delta C_T$ values.

Transcription of the iNOS gene in response to the various treatments and culture times was modeled using transformed qRT-PCR data. Data reduction was performed using the ΔΔCt method (Ct indicates primer efficiency (Table 4) adjusted threshold cycle values were used) with Rn18s as the housekeeping gene. Given the large efficiency value associated with the β-actin primer pair, data associated with its gene expression were taken as erroneous and disregarded. Fold change values in mRNA expression as compared to the basal time zero expression level are shown in FIG. 10. An up regulation of iNOS was seen for all treatment groups by at least 24 hours, the time point which corresponded with each treatment's maximum measured expression level. LPS, and possibly F2−, treatment(s) induced an early response showing increased transcription after only five hours. iNOS expression levels fell in all groups between the 24 and 48 hour time points. F1+, F2+, and F2− material groups had returned to or dropped below the basal expression level by 48 hours.

Response surface modeling of the linearized ΔCt values indicated significant effects of all factors and accounted for 81% of the variance ($R^2$-value). The covariate material parameter demonstrated a significance effect in the model ($p<0.0001$). Time was found to significantly affect the data as a second-order parameter in which both the linear and more so the quadratic parameters were significant ($p=0.0078$ and 0.0017, respectively). The quadratic parameter for time and the linear material covariate were most influential in the model as their values were estimated at −0.375 and 0.448 (all variables coded for comparison), respectively, as compared to the much smaller linear time parameter estimation of −0.072 (variables coded for comparison). Additionally, canonical analysis of the model demonstrated negative eigenvalues, corresponding to a maximum linearized ΔCt response of 0.62 on the surface map at the coded independent stationary point value of −0.096, corresponding to 21.7 hours of exposure.

Figure 12:
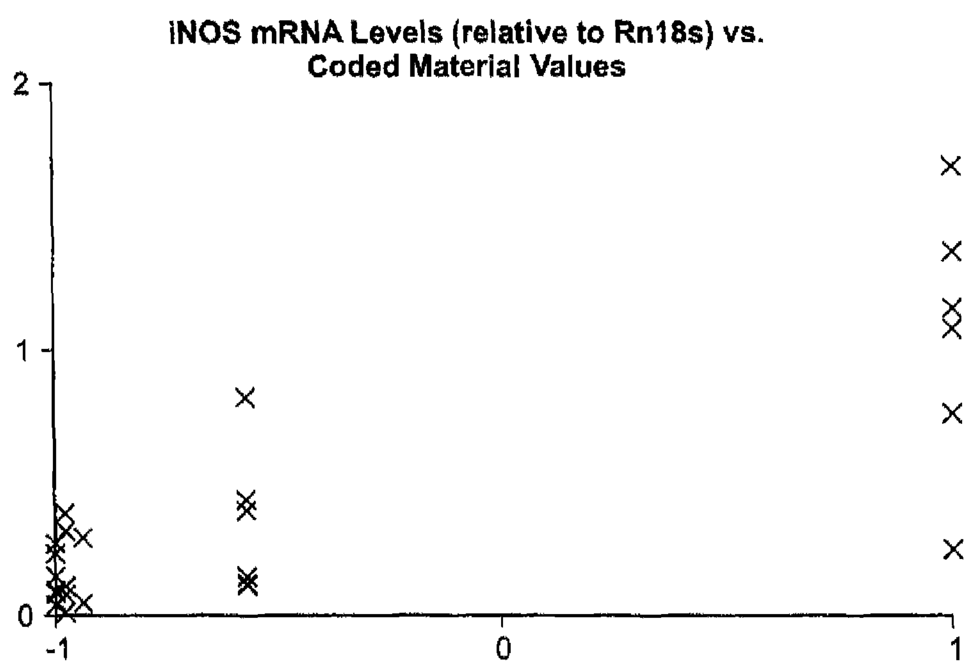
FIG. 12 shows linearized $\Delta C_T$ measures for iducible-nitric oxide synthase (iNOS) with Rn18s histone gene taken as a housekeeping gene plotted against coded treatment values is shown (F1+=−1; F2+=−0.98; Basal (time zero)=−0.94; F2−=−0.57; LPS=1). Coded values span −1 to 1 and are proportionally spaced based on the mean response differences. A linear dependence of material is evident after performing this linear transformation of the categorical treatment data and was included as such in the formal analysis. Upregulation of iNOS transcription is evident for the F2− and LPS treatment groups.
Figure 13:
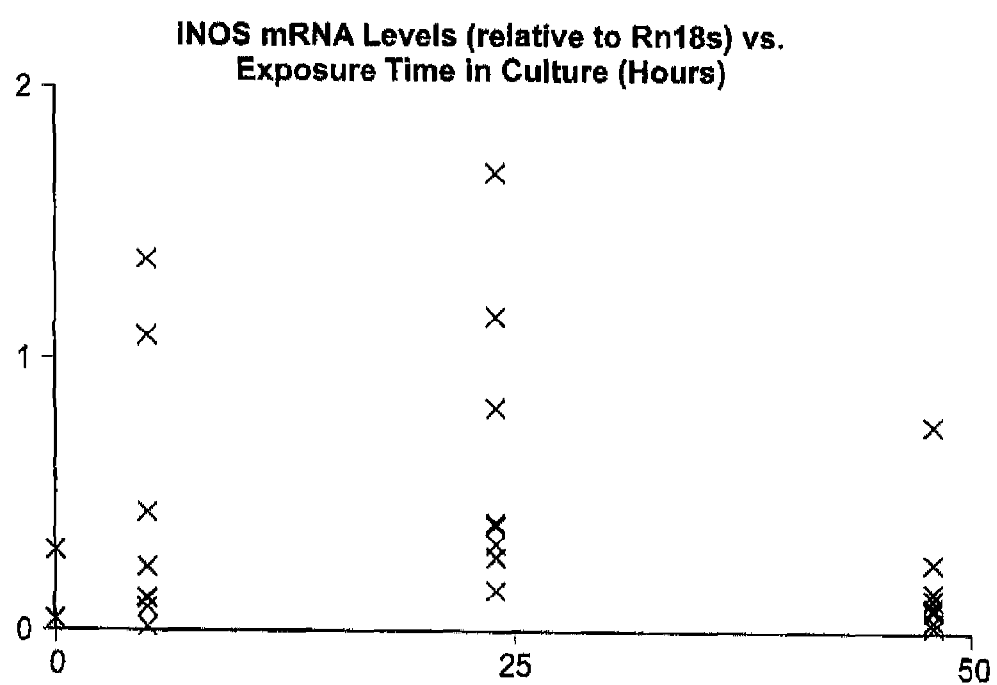
FIG. 13 shows linearized $\Delta C_T$ measures for iNOS with Rn18s taken as a housekeeping gene plotted against exposure time is shown. Given the average relative increase in iNOS by the 24 hour time point followed by down regulation back to levels comparable to that of basal (time zero), a parabolic function was chosen to describe this response in the formal analysis.

Now refereeing to FIGS. 12 & 13, show the linearized ΔCt data in 2D plots. FIG. 12 shows how coding the categorical treatment variable allowed for linearization in this dimension; linearized ΔCt values increase (iNOS up regulation) from −1 (F1+) to 1 (LPS). The data are somewhat skewed to the left of the 24 hour time point which was also reflected in the response surface model which demonstrated a maximum value at 21.7 hours of exposure time.

FIG. 13 demonstrates the parabolic dependency with time of the linearized ΔCt data as values obviously peak at the 24 hours. Although, time is also coded in the response surface procedure so that parameter estimates may be compared among different variables directly in taking variable value ranges into consideration. This rise and fall nature of the gene expression may be related to either an endocytosis process in which inflammatory agents are being depleted, receptor internalization and down-regulation, or receptor desensitization from over-activation of the signal transduction pathway. These graphs clearly show the dependent linearization of the data against material, the independent covariate, and the parabolic response of the data in regards to time. These observations validate the selection of a second-order response surface model with incorporation of a linear covariate, hence a 3D model.

TABLE 4

Primer Pairs Used for qRT-PCR
Primer Pairs Used for qRT-PCR

| Gene | direction | nucleotide sequences | efficiency (E) |
|---|---|---|---|
| iNOS | sense | 5'-TAG GTC GAT GCA CAA CTG GGT GAA-3'; SEQ ID NO. 1 | 1.71 |
| | anti-sense | 5'-TCT TTG ACG CTC GGA ACT GTA GCA-3'; SEQ ID NO. 2 | |
| Rn18s | sense | 5'-TAT TGC TCA ATC TCG GGT GC TGA-3'; SEQ ID NO. 3 | 1.65 |
| | anti-sense | 5'-CCA GAG CGA AAG CAT TTG CCA AGA-3' SEQ ID NO. 4 | |
| B--Actin | sense | 5'-ACT CCT GCT TGC TGA TCC ACA TCT-3'; SEQ ID NO 5 | 2.64 |
| | anti-sense | 5'-TCG TAC CAC AGG CAT TGT GAT GGA-3'; SEQ ID NO. 6 | |

Note:
Primer pairs were designed using Integrated DNA Technologies' on-line PRIMERQUEST software and NIH's GENBANK. Data associated with B--Actin measures were discarded due to poor efficiency.

Figure 11:
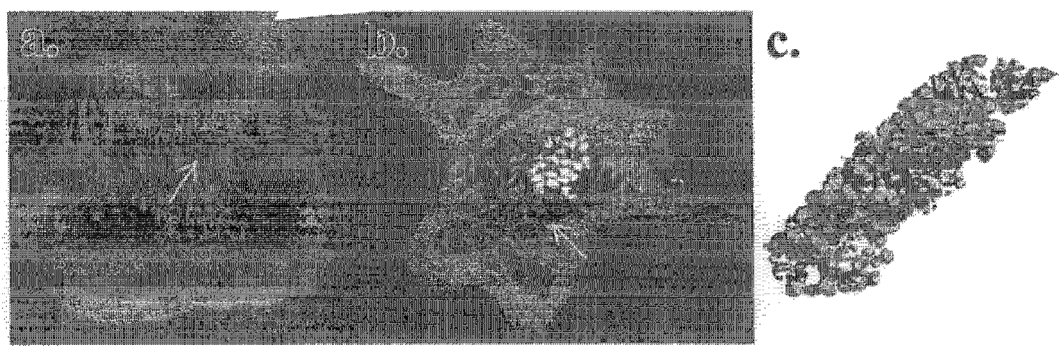
FIG. 11. Shows μCT radiographic (a. and b.) and rendered (c.) images of injection delivered and in situ cured F1+ material within the cancellous region of a rat Ca-2 vertebrae. B-tricalcium phosphate granules can be seen as the material with higher radiopacity and indicated implant localization. Morselized trabeculae can be seen adjacent to the implant (arrows), indicating cohesiveness of the curing material as it is being delivered. a. Radiographic image showing anterior-posterior section. b. Radiographic image showing transverse section. c. Rendered image of implanted material. 22.8% (v/v) was calculated for B-tricalcium phosphate granules compared to the formulation theoretical value of 20% (v/v), indicated homogenization of the mixed material is preserved during injection.

Now referring to FIGS. 11A-11C, injection delivery of F1+ into rat Ca-2 and -3 vertebrae through a burred hole was successfully accomplished, and the β-tricalcium phosphate component was clearly distinguishable from the native bone due to a higher radiopacity. FIG. 11C shows the 3D rendering of delivered material in situ; automated software analysis of this bolus calculated a β-tricalcium phosphate volume percentage of 22.8%, only 2.8% higher than the theoretical formulation calculations (Table 4). A low degree of anisotropy (DA) value of 1.04 was also determined with the software and is in agreement of the spherical nature of the β-tricalcium phosphate granules (DA=1 being a perfect sphere). Images and calculations showed that the biocomposite was able to be localized as an injected bolus within cancellous bone, a minimally invasive delivery procedure.

Inflammatory responses inherent to the base material were found and could be modulated through incorporation of platelet releasate. Differences in hydrogel weight percent (2 vs. 8%) and/or calcium phosphate granule volume percent (20 vs. 10%) allowed for tuning the response associated with platelet releasate-associated growth factor elution. Tunabliity from completely suppressing the inflammatory response to augmenting the response was observed through varied elution profiles of both releasate-derived bioagents and impurities inherent to alginate. A 2.5-fold up regulation of inducible-nitric oxide synthase gene expression followed by a 10-fold increase in nitrite media levels was inducted by including of releasate within the 8 wt %/10 vol % formation and was comparable to an endotoxin positive control. Whereas, near complete elimination of inflammation was seen when releasate was included within the 2 wt %/20 vol % formulation.

A number of embodiments of the invention have been described. Nevertheless, it will be understood that various modifications may be without departing from the spirit and scope of the invention.

The invention claimed is:

1. An injectable in situ curing biomaterial composite product made by a process comprising the steps of: admixing an alginate solution with nonporous β-tricalcium phosphate aggregates, in a sufficient amount to allow for polymerization after injection of said biomaterial composite product to form a hydrogel having from between 10 to 20 percent by volume of β-tricalcium phosphate.

2. The product of claim 1 wherein said aggregates have a diameter distribution of between 125-150 μm.

3. The product of claim 1 wherein said a hydrogel has from between 2 to 8 weight percent of alginate.

4. The product of claim 1 further comprises adding a sufficient amount of calcium sulfate to said β-tricalcium phosphate before admixing said solution, wherein a rate of polymerization is increased and a gel time is lowered.

5. The product of claim 1 further comprises adding a sufficient amount of platelet releasate to said solution, wherein the product in vivo can stimulate platelet releasate bioactivity.

6. The product of claim 5 wherein a sufficient amount of the platelet releasate provide at least 50 percent by volume of the hydrogel.

7. The product of claim 1 further comprises adding a sufficient amount of alpha hydroxy carboxylic acids or salts thereof to increase the flowability of the hydrogel.

8. The product of claim 7 wherein the alpha hydroxy carboxylic is trisodium citrate.

9. The product of claim 1 further comprising a bioactive agent.

10. The product of claim 9 wherein the bioactive agent is derived from platelets and said bioactive agent comprises at least 50 percent by volume of the hydrogel portion of the product.

11. The product of claim 9 wherein said nonporous β-tricalcium phosphate aggregates have a diameter distribution of 125-150 μm.

12. The product of claim 9 wherein the hydrogel has from between 2 to 8 weight percent of alginate and the composite has from between 10 percent to 20 percent by volume of β-tricalcium phosphate.

13. A kit comprising: a first mixing container containing an alginate solution, a second mixing container containing between 10 to 20 percent by volume of β-tricalcium phosphate, wherein said first mixing container and said second mixing container are connected and wherein said alginate solution and said β-tricalcium phosphate upon mixing form a hydrogel; and a needle of not more than 16 gauge in dimension wherein said needle is attachable to either the first or the second container and wherein said needle is sized to extrude said hydrogel from said first or second container.

14. The kit of claim 13 further comprising a third mixing container, attachable to either the first or second container, with a bioactive agent.

15. A method to facilitate bone repair comprising administering to a mammalian subject in need of such bone repair treatment an effective amount of the composition of claim 1 to a site in said subject.

16. The method of claim 15 wherein said site is selected from the group consisting of subchondral, osteochondral and cancellous bone.

17. The method of claim 16 wherein said bone is adjacent to a structure selected from the group consisting of: vertebral endplates and annulus fibrosus of a spinal disc.

18. The method of claim 15 wherein said site is adjacent to cartilage.

19. The method of claim 18 wherein said site is selected from the group consisting of articular and fibrocartilage.

20. The method of claim 18 wherein said cartilage is selected from the group consisting of: upper and lower vertebral endplates and the annulus fibrosus of a spinal disc.

21. The method of claim 15 wherein the repair is bone remodeling, similar to hematoma-induced fracture healing.

22. A method to facilitate bone repair comprising administering to a mammalian subject in need of such bone repair treatment an effective amount of the composition of claim 9 to a site in said subject.

23. The method of claim 22 wherein said site is selected from the group consisting of: subchondral, osteochondral and cancellous bone.

24. The method of claim 23 wherein said bone is adjacent to a structure selected from the group consisting of: vertebral endplates and annulus fibrosus of a spinal disc.

25. The method of claim 22 wherein said site is cartilage or adjacent to cartilage.

26. The method of claim 22 wherein said site is selected from the group consisting of articular and fibrocartilage.

27. The method of claim 25 wherein said cartilage is selected from the group consisting of: upper and lower vertebral endplates and the annulus fibrosus of a spinal disc.

28. The method of claim 22 wherein the repair is bone remodeling, similar to hematoma-induced fracture healing.

29. A process to release a bioactive agent to a site in a subject comprising: administering an effective amount of an injectable in situ curing biomaterial composite to the site in the subject, said material prepared by a process comprising the steps of: admixing an alginate solution with a sufficient amount of a bioactive agent and at least one calcium salt, in a sufficient amount to allow for polymerization after injection of said biomaterial composite and to form a hydrogel wherein the calcium salt is a nonporous aggregate of β-tricalcium phosphate and said biomaterial composite is comprised of between 10 to 20 percent by volume of β-tricalcium phosphate.

30. The process of claim 29 wherein said bioactive agent is angiogenic and the site is adjacent to cartilage.

31. The process of claim 29 wherein said bioactive agent is a growth factor and the site is selected from the group consisting of: bone fracture, bone void and bone nonunion.

32. The process of claim 29 wherein said site is selected from the group consisting of: subchondral, osteochondral, cancellous bone, and cartilage.

33. The process of claim 29 wherein said bioactive agent is derived from platelets.

34. The process of claim 33 wherein said bioactive agent is platelet releasate and the bioactive agent comprises at least 50 percent by volume of the hydrogel.

35. The process of claim 29 further comprises adding a sufficient amount of alpha hydroxy carboxylic acids or salts thereof to increase the flowability of the hydrogel.

36. The process of claim 35 wherein the alpha hydroxy carboxylic is trisodium citrate.

37. A method of treating a condition whose effects can be reduced by stimulating the cellular responses induced by platelet releasate exposure comprising: administering to a subject in need of such treatment a therapeutically effective amount of a composition comprising: an injectable in situ curing hydrogel biomaterial composite comprising an alginate gel having embedded therein a nonporous β-tricalcium phosphate solid phase, and a bioactive agent, wherein said bioactive agent is derived from platelets and said biomaterial composite is comprised of between 10 to 20 percent by volume of β-tricalcium phosphate.

38. The method of claim 37 wherein the therapeutically effective amount of the biomaterial composite composition comprises an effective amount of the biomaterial composite composition to stimulate the cellular responses induced by platelet releasate exposure.

39. The method of claim 37 wherein the therapeutically effective amount of the biomaterial composite composition comprises an effective amount of the biomaterial composite composition to modulate an inflammatory response.

40. The product of claim 10 wherein the bioactive agent is platelet releasate.

* * * * *

UNITED STATES PATENT AND TRADEMARK OFFICE

CERTIFICATE OF CORRECTION

PATENT NO. : 8,404,256 B2
APPLICATION NO. : 13/462075
DATED : March 26, 2013
INVENTOR(S) : Jonathan Dempsey McCanless It is certified that error appears in the above-identified patent and that said Letters Patent is hereby corrected as shown below:

Title Page, item [75] inventor: "Haggard; Warren Ollver" should read as "Haggard; Warren Oliver".

Title Page, item [75] inventors address: "Bartlets" should read as "Bartlett".

Signed and Sealed this
Thirtieth Day of April, 2013

Teresa Stanek Rea
*Acting Director of the United States Patent and Trademark Office*